United States Patent
Tsukabayashi et al.

(10) Patent No.: US 8,821,797 B2
(45) Date of Patent: Sep. 2, 2014

(54) HYDROGEN DETECTION SYSTEM

(75) Inventors: Shunji Tsukabayashi, Saitama (JP);
Hidetoshi Oishi, Saitama (JP);
Kazuhiro Okajima, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 214 days.

(21) Appl. No.: 13/364,757

(22) Filed: Feb. 2, 2012

(65) Prior Publication Data

US 2012/0201715 A1  Aug. 9, 2012

(30) Foreign Application Priority Data

Feb. 3, 2011  (JP) .................................. 2011-021573

(51) Int. Cl.
*G01N 15/06* (2006.01)

(52) U.S. Cl.
USPC .................. 422/83; 422/88; 422/90; 422/91; 422/92; 422/98; 73/23.2; 73/23.21; 73/23.31

(58) Field of Classification Search
USPC ............... 422/83, 88, 90, 91, 92, 98; 73/23.2, 73/23.21, 23.31
See application file for complete search history.

(56) References Cited

U.S. PATENT DOCUMENTS

| 2005/0155405 A1 | 7/2005 | Sasaki et al. |
| 2006/0113198 A1 | 6/2006 | Sasaki et al. |
| 2009/0035184 A1 | 2/2009 | Koda et al. |

FOREIGN PATENT DOCUMENTS

| JP | 2003-329631 A | 11/2003 |
| JP | 2007-048578 A | 2/2007 |
| WO | WO2007/099933 A1 | 9/2007 |

OTHER PUBLICATIONS

German Search Report application No. 10 2012 201 647.3 dated Sep. 17, 2012.

*Primary Examiner* — Brian J Sines
(74) *Attorney, Agent, or Firm* — Squire Patton Boggs (US) LLP

(57) ABSTRACT

A hydrogen detection system can include an exposed detection element made of a catalytic metal which burns hydrogen so as to generate combustion heat. A hydrogen sensor can detect a hydrogen concentration based on a detected value of the detection element. A heating unit can heat the detection element. A hydrogen storage unit is included, and a hydrogen guiding pipe can guide the hydrogen from the hydrogen storage unit to the detection element. A flow rate adjusting device is attached to the hydrogen guiding pipe, and adjusts a flow rate of the hydrogen. A first dilution unit can dilute the hydrogen from the hydrogen storage unit with a dilution gas, and a controller can control the heating unit and the flow rate adjusting device.

13 Claims, 13 Drawing Sheets

HYDROGEN DETECTION SYSTEM

CROSS REFERENCE TO RELATED APPLICATION

The present application claims benefit of the filing date of Japanese Patent Application No. 2011-021573 filed on Feb. 3, 2011 which is incorporated herein by reference.

BACKGROUND OF THE INVENTION

1. Field of the Invention

The present invention relates to a hydrogen detection system.

2. Description of the Related Art

In recent years, a fuel cell using hydrogen as a fuel gas has attracted attention as a clean energy source, and a fuel cell vehicle having the fuel cell as an energy source for driving the vehicle has been developed. Also, the fuel cell vehicle is provided with a hydrogen sensor for detecting leakage of hydrogen.

As the hydrogen sensor, a catalytic combustion type hydrogen sensor which has a simple structure and can be miniaturized easily is used. However, with respect to the hydrogen sensor, it is well known that if vapor of a silicon compound exists in an atmosphere of an operational environment, the silicon compound adheres to a detection element and a detection sensitivity deteriorates over time (silicon (Si) poisoning).

For this reason, a technique for covering a poisoned detection element by a silicon trapping layer has been proposed (see WO 2007/099933 A1).

SUMMARY OF THE INVENTION

However, since the silicon compound merely adheres to the silicon trapping layer in the atmosphere in WO 2007/099933 A1, it is thought that an adhering mass of the silicon compound is limited. For this reason, a length of time before the detection sensitivity deteriorates can be elongated, the detection sensitivity finally deteriorates.

Therefore, an object of the present invention is to provide a hydrogen detection system for recovering a hydrogen detection sensitivity of a hydrogen sensor.

In order to achieve the above object, the present invention provides a hydrogen detection system, comprising: an exposed detection element made of a catalytic metal which burns hydrogen so as to generate combustion heat; a hydrogen sensor for detecting a hydrogen concentration based on a detected value of the detection element, the value varies corresponding to the combustion heat; a heating unit for heating the detection element; a hydrogen storage unit for storing a high-concentration hydrogen; a hydrogen guiding pipe for guiding the hydrogen from the hydrogen storage unit to the detection element; a flow rate adjusting device which is attached to the hydrogen guiding pipe and adjusts a flow rate of the hydrogen; a first dilution unit for diluting the hydrogen from the hydrogen storage unit with a dilution gas at a position between the flow rate adjusting device and the detection element; and a controller for controlling the heating unit and the flow rate adjusting device, wherein the controller performs a sensitivity recovery process by controlling a concentration of hydrogen supplied from the first dilution unit to the detection element using the flow rate adjusting device so that a temperature of the detection element heated by the heating unit is equal to or greater than a desorption temperature at which silicon adhering to the detection element is desorbed by the combustion heat of the hydrogen when a sensitivity recovery of the hydrogen sensor is required.

Here, "an exposed detection element made of a catalytic metal which burns hydrogen so as to generate combustion heat" means that the detection element itself is made of the catalytic metal and that the detection element is exposed so that the hydrogen directly contacts the detection element so as to burn it.

Also, "so that a temperature of the detection element heated by the heating unit is equal to or greater than a desorption temperature at which silicon adhering to the detection element is desorbed" means that the detection element is heated to a range of the desorption temperature at which the silicon is desorbed in an embodiment described later.

According to the hydrogen detection system, the controller performs the sensitivity recovery process by controlling the concentration of the hydrogen supplied from the first dilution unit to the detection element using the flow rate adjusting device so that the temperature of the detection element heated by the heating unit is equal to or greater than the desorption temperature at which the silicon adhering to the detection element is desorbed by the combustion heat of the hydrogen when the sensitivity recovery of the hydrogen sensor is required.

In this way, when the sensitivity recovery of the hydrogen sensor is required, the temperature of the detection element is raised to or above the desorption temperature, the silicon adhering to the detection element is intentionally desorbed, and the hydrogen detection sensitivity of the hydrogen sensor (the detection element) can be recovered. Therefore, the hydrogen concentration can be detected by the hydrogen sensor for a long time.

Also, in the hydrogen detection system, the controller preferably commands the heating unit to heat the detection element to a standby temperature, and the standby temperature is preferably a temperature obtained by subtracting a temperature rise caused by a combustion of the hydrogen at the time of requirement of the sensitivity recovery from the desorption temperature.

According to the hydrogen detection system, the controller commands the heating unit to heat the detection element to the standby temperature. The standby temperature is set to a temperature obtained by subtracting the temperature rise caused by the combustion of the hydrogen at the time of requirement of the sensitivity recovery from the desorption temperature. The controller commands the heating unit in consideration of the temperature rise caused by the combustion of the hydrogen at the time of requirement of the sensitivity recovery (i.e., the controller adjusts the standby temperature). In other words, the standby temperature is set corresponding to the hydrogen concentration diluted by the first dilution unit, and the heating unit heats the detection element to the standby temperature. As a result, when the sensitivity recovery is required, the temperature of the detection element does not rise too much, and does not exceed the desorption temperature too much.

Also, since the standby temperature is adjusted as described above, an energy (an electric power, etc.) consumed by the heating unit can be reduced.

Also, in the hydrogen detection system, the hydrogen sensor preferably comprises a power supplying unit for supplying power to the detection element, and detects the hydrogen concentration based on an increase in a resistor value of the detection element caused by the combustion of the hydrogen, and the heating unit preferably comprises the power supplying unit, and the temperature of the detection element is raised by supplying power to the detection element.

According to the hydrogen detection system, the power supplying unit of the hydrogen sensor can be used as the heating unit. For this reason, the heating unit (a heater, etc.) dedicated for heating the detection element is not needed separately, and a structure of the hydrogen detection system is simplified.

Also, in the hydrogen detection system, the flow rate adjusting device is preferably provided with a valve unit capable of keeping a predetermined open state, and the controller preferably controls the concentration of the hydrogen supplied to the detection element by controlling an open time/close time of the valve unit.

According to the hydrogen detection system, the controller controls the concentration of the hydrogen supplied to the detection element by controlling the open time/close time of the simple valve unit (the flow rate adjusting device) capable of keeping the predetermined open state.

Also, in the hydrogen detection system, the flow rate adjusting device is preferably provided with the valve unit whose opening degree can desirably adjustable, and the controller preferably controls the concentration of the hydrogen supplied to the detection element by controlling the opening degree of the valve unit.

According to the hydrogen detection system, the controller controls the concentration of the hydrogen supplied to the detection element by controlling the opening degree of the simple valve unit (a flowing controller) whose opening degree can desirably adjustable.

Also, in the hydrogen detection system, the controller preferably begins a present sensitivity recovery process after a first predetermined time during which the hydrogen concentration in the first dilution unit falls to a predetermined concentration has elapsed since a previous sensitivity recovery process was completed.

According to the hydrogen detection system, the controller begins the present sensitivity recovery process after the first predetermined time during which the hydrogen concentration in the first dilution unit falls to the predetermined concentration since the previous sensitivity recovery process was completed.

That is, if the hydrogen concentration is kept high in the first dilution unit for a while after the previous sensitivity recovery process was completed and the present sensitivity recovery process is continuously begun, the concentration of the hydrogen supplied to the detection element is too high, and the temperature of the detection element may be raised too much by the combustion heat of the hydrogen.

For this reason, the first dilution unit dilutes the hydrogen since the previous sensitivity recovery process was completed. After the first predetermined time during which the hydrogen concentration falls to the predetermined concentration has elapsed, the present sensitivity recovery process is begun. In this way, the concentration of the hydrogen supplied to the detection element does not rise too much, and the temperature of the detection element is not unexpectedly raised by the combustion heat of the hydrogen.

Also, in the hydrogen detection system, the controller preferably repeats the sensitivity recovery process every second predetermined time which is equal to or greater than the first predetermined time.

According to the hydrogen detection system, since the controller repeats the sensitivity recovery process every second predetermined time which is equal to or greater than the first predetermined time, a sensitivity of the hydrogen sensor can be recovered every second predetermined time.

Also, since the second predetermined time is equal to or greater than the first predetermined time, higher-than-expected-concentration hydrogen is not supplied to the detection element and the temperature of the detection element is not raised higher than expected by the combustion heat of the hydrogen if the sensitivity recovery process is repeated every second predetermined time.

Also, the hydrogen detection system preferably comprises a dilution gas flowing unit (a compressor 131 in an embodiment described later) for flowing the dilution gas through the first dilution unit, and the controller preferably commands the dilution gas flowing unit to supply the dilution gas after the sensitivity recovery process was completed.

According to the hydrogen detection system, since the controller commands the dilution gas flowing unit to supply the dilution gas after the sensitivity recovery process is completed, the hydrogen concentration in the first dilution unit falls rapidly. In this way, the next sensitivity recovery process can be executed rapidly.

Also, in the hydrogen detection system, the hydrogen sensor is preferably attached to a cathode exhaust gas flow path through which a cathode exhaust gas is supplied from a cathode of the fuel cell, the hydrogen guiding pipe preferably joins the cathode exhaust gas flow path which is upstream of the hydrogen sensor, the first dilution unit is preferably the cathode exhaust gas flow path between the hydrogen guiding pipe and the hydrogen sensor, and the dilution gas is preferably the cathode exhaust gas.

According to the hydrogen detection system, since the cathode exhaust gas supplied from the cathode of the fuel cell is used as the dilution gas, there is no need to separately provide a dilution gas supplying unit, the structure of the system is simplified, and the hydrogen detection system is made to be cheap.

Also, in the hydrogen detection system, an anode exhaust gas flow path which exhausts an anode exhaust gas supplied from an anode of the fuel cell preferably joins the cathode exhaust gas flow path which is upstream of the hydrogen guiding pipe, the anode exhaust gas flow path is preferably provided with a purge valve which is open when the anode exhaust gas is exhausted, and the controller preferably begins the sensitivity recovery process after a third predetermined time during which the hydrogen concentration in the first dilution unit falls to a predetermined concentration has elapsed since the purge valve was closed.

According to the hydrogen detection system, since the controller begins the sensitivity recovery process after the third predetermined time during which the hydrogen concentration in the first dilution unit falls to the predetermined concentration has elapsed since the purge valve is closed, the concentration of the hydrogen supplied to the detection element does not rise too much, and the temperature of the detection element is not unexpectedly raised by the combustion heat of the hydrogen.

Also, in the hydrogen detection system, the cathode exhaust gas flow path which is downstream of the hydrogen sensor is preferably provided with a second dilution unit.

According to the hydrogen detection system, since the cathode exhaust gas flow path which is downstream of the hydrogen sensor is provided with the second dilution unit, the high-concentration hydrogen can be supplied to the detection element in order to increase the temperature rise caused by the combustion of the hydrogen when the sensitivity recovery process is performed. In this way, an amount of heat applied to the detection element by the heating unit can be reduced, and the energy consumed by the heating unit (an electric power, etc.) can be reduced.

Also, in the hydrogen detection system, the hydrogen sensor is preferably placed in a space opened to the atmosphere, the first dilution unit is a space for dilution opened to the atmosphere and which is placed between a downstream end of the hydrogen guiding pipe and the hydrogen sensor, and the dilution gas is preferably the atmosphere.

According to the hydrogen detection system, the first dilution unit is the space for dilution opened to the atmosphere and which is placed between the downstream end of the hydrogen guiding pipe and the hydrogen sensor, and the dilution gas is the atmosphere. Therefore, there is no need to provide a special supplying unit of the dilution gas, the structure of the system is simplified, and the hydrogen detection system is made to be cheap.

Also, the hydrogen detection system is preferably mounted on a fuel cell vehicle which has a fuel cell and is driven by an electric power generated by the fuel cell, and the hydrogen storage unit preferably supplies the hydrogen to the fuel cell as the fuel gas.

According to the hydrogen detection system, a durability of the hydrogen sensor is improved.

Also, the hydrogen storage unit supplies the hydrogen to the fuel cell as the fuel gas. In other words, a hydrogen tank mounted on the fuel cell vehicle is used as a hydrogen storage unit of the high-concentration hydrogen for the sensitivity recovery process. Therefore, the sensitivity recovery process can appropriately be performed by only the fuel cell vehicle.

DESCRIPTION OF PREFERRED EMBODIMENTS

Hereinafter, with reference to FIGS. 1-13, one embodiment of the present invention will be explained.

<<Structure of Fuel Cell Vehicle>>

Figure 1:
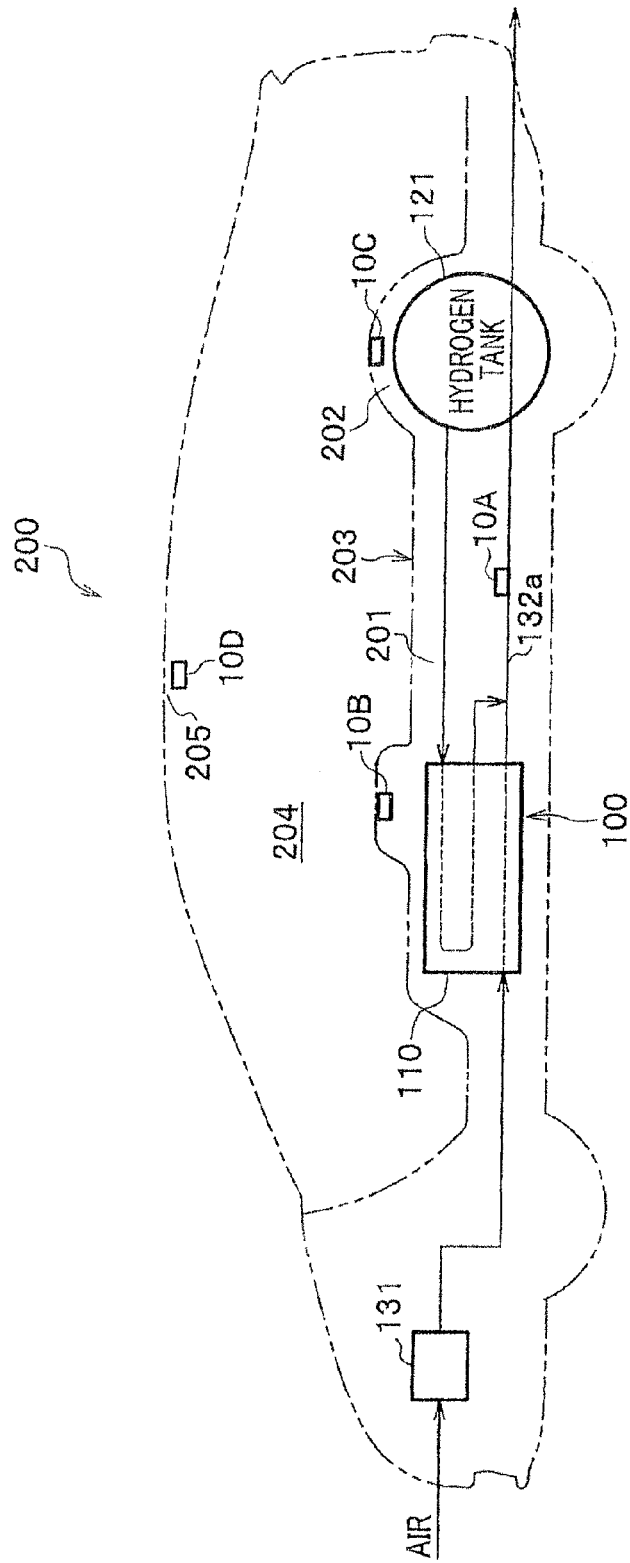
FIG. 1 is a side view of a fuel cell vehicle according to an embodiment of the present invention.

As shown in FIG. 1, a fuel cell vehicle 200 is provided with a fuel cell system 100 comprising a PEFC (Polymer Electrolyte Fuel Cell) type fuel cell stack 110, a hydrogen tank (i.e., a hydrogen storage unit) 121, and hydrogen sensors 10A-10D, and is traveled by rotating a driving motor (not shown) using an electric power generated by the fuel cell stack 110.

The fuel cell stack 110 is placed in a center tunnel 201, and the hydrogen tank 121 is placed in a tank compartment 202. The center tunnel 201 is formed by protruding a central portion of a floor panel 203 in the vehicle width direction, and is a slender space in the vehicle front-rear direction. The tank compartment 202 is formed by protruding a rear side portion of the floor panel 203 corresponding to a shape of the hydrogen tank 121, and is a cylindrical space extending in the vehicle width direction.

As described later, the hydrogen sensor 10A is attached to a pipe (i.e., a cathode exhaust gas flow path) 132a, detects a hydrogen concentration in a cathode exhaust gas, and outputs the hydrogen concentration to an ECU 150 (see FIG. 2).

Figure 2:
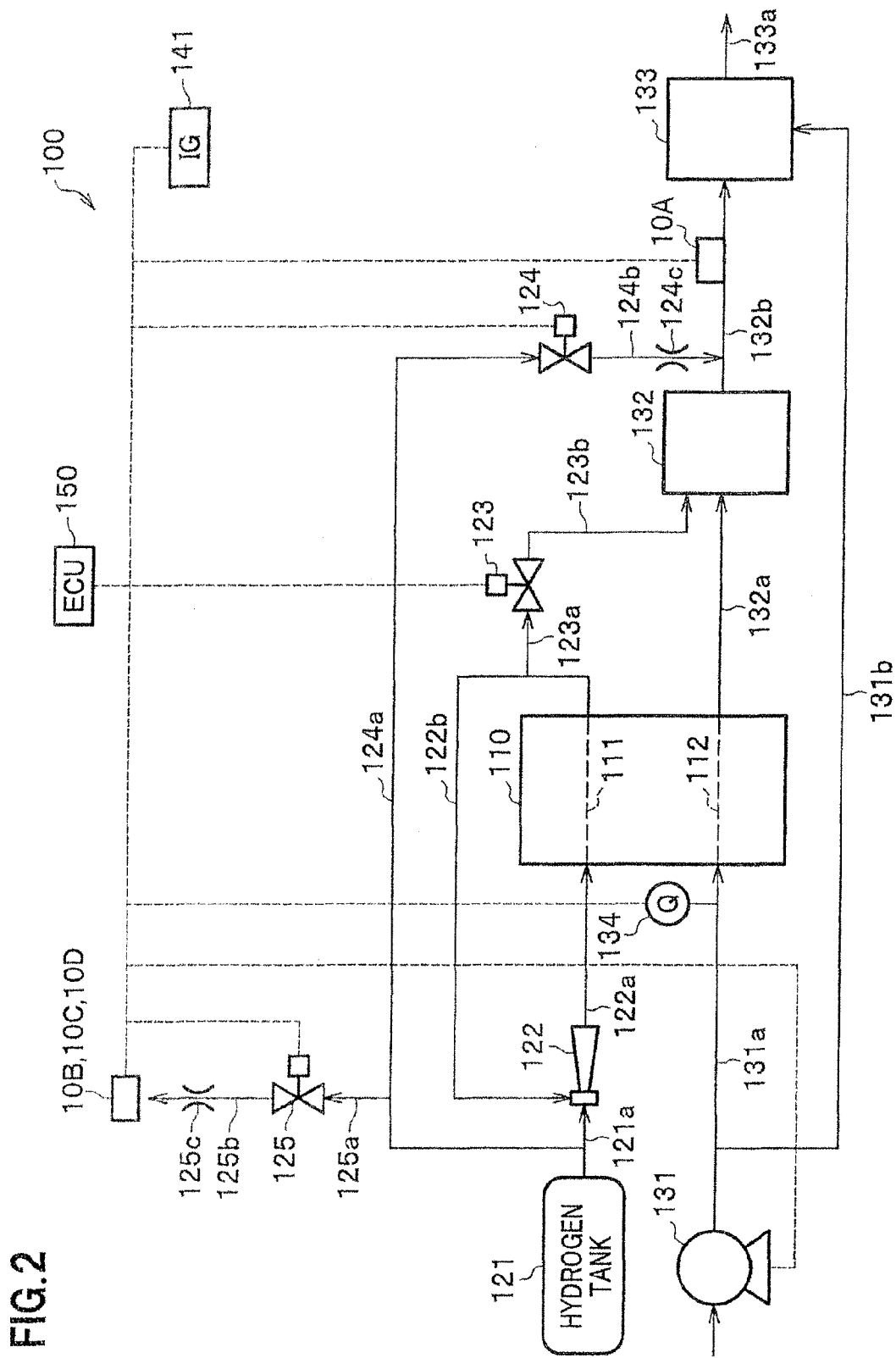
FIG. 2 is a block diagram of a fuel cell system (a hydrogen detection system) according to the embodiment.

The hydrogen sensor 10B is attached to a bottom face of the floor panel 203 over the fuel cell stack 110, detects the concentration of the hydrogen which leaks out of the fuel cell stack 110, etc. and resides in the center tunnel 201, and outputs the concentration to the ECU 150 (see FIG. 2).

The hydrogen sensor 10C is attached to the bottom face of the floor panel 203 over the hydrogen tank 121, detects the concentration of the hydrogen which leaks out of the hydrogen tank 121, etc. and resides in the tank compartment 202, and outputs the concentration to the ECU 150 (see FIG. 2).

The hydrogen sensor 10D is attached to a roof lining 205 over the vehicle compartment 204, detects the concentration of the hydrogen which resides in the vehicle compartment 204, and outputs the concentration to the ECU 150 (see FIG. 2).

That is, the hydrogen sensors 10B-10D are placed in spaces such as the center tunnel 201, the tank compartment 202, and the vehicle compartment 204, etc. which are opened to the atmosphere.

<<Fuel Cell System>>

As shown in FIG. 2, the fuel cell system 100 is a system into which a hydrogen detection system 1 is integrated, and is provided with a fuel cell stack 110 (a fuel cell), an anode system for supplying/exhausting the hydrogen (the fuel gas) to/from an anode of the fuel cell stack 110, a cathode system for supplying/exhausting an air (an oxidizing gas) to/from a cathode of the fuel cell stack 110, the hydrogen sensors 10A-10D, and an ECU 150 (an Electronic Control Unit, a controller) for controlling thereof.

<Fuel Cell Stack>

The fuel cell stack 110 is a stack of a plurality of (e.g., 200-400 pieces of) solid polymer type single cells connected in series. The single cell is provided with a MEA (Membrane Electrode Assembly) and two conductive separators for sandwiching the MEA. The MEA is provided with an electrolyte membrane (a solid polymer membrane) comprising a monatomic proton exchange membrane, etc., and electrodes (an anode and a cathode) for sandwiching the electrolyte membrane.

The anode and the cathode include a conductive porous body such as a carbon paper, etc., and a catalyst (Pt, Ru, etc.) which is supported by the conductive porous body and causes an electrode reaction at the anode and the cathode.

Channels for supplying the hydrogen or the air to all surfaces of each of the MEA and through holes for supplying/exhausting the hydrogen or the air to/from all of the single cells are formed on each of the separators, and these channels and through holes serve as an anode flow path (a fuel gas flow path) 111 and a cathode flow path (an oxidizing gas flow path) 112.

<Anode System>

The anode system is provided with a hydrogen tank (a hydrogen storage unit) 121, an ejector 122, an normal closed-type purge valve 123, and normal closed-type cleaning valves (flow rate adjusting devices) 124, 125 which are opened when cleaning of the hydrogen sensors 10A, 10B (10C, 10D) is performed (when the sensitivity recovery process is performed).

The hydrogen tank 121 is a tank for storing a high concentration (high purity) hydrogen under a high pressure (e.g., 30-70 MPa). Also, the hydrogen in the hydrogen tank 121 is supplied to the anode flow path 111 through a pipe 121a, an ejector 122, and a pipe 122a. The ejector 122 is a device (a vacuum pump) for generating a negative pressure using the hydrogen from the hydrogen tank 121 and circulating the hydrogen by sucking the anode exhaust gas containing the below described hydrogen using this negative pressure.

In addition, the pipe 121a is provided with an normal closed-type shutdown valve (not shown) and a pressure reducing valve (regulator) (not shown) toward its downstream. The shutdown valve is opened in accordance with commands from the ECU 150 when the fuel cell system 100 (the fuel cell vehicle 200) is active (when an IG 141 is turned ON). Also, the pressure reducing valve reduces a pressure of the hydrogen from the hydrogen tank 121 appropriately.

The anode exhaust gas containing an unreacted hydrogen exhausted from the anode flow path 111 is supplied to an inlet of the ejector 122 through the pipe 122b (a hydrogen circulation line).

The pipe 122b is connected to a below described dilution box 132 via the pipe 123a, the purge valve 123, and the pipe 123b. Also, when the purge valve 123 is opened in accordance with commands from the ECU 150 at a predetermined open time, the anode exhaust gas containing the unreacted hydrogen is exhausted to the dilution box 132, and a generating capacity of the fuel cell stack 110 is recovered.

In addition, for example, the ECU 150 is set to determine to open the purge valve 123 if the lowest voltage (the lowest cell voltage) of voltages of the single cell of the fuel cell stack 110 is equal to or less than a predetermined single cell voltage. Also, the ECU 150 monitors voltages of the plurality of plurality of the single cells via a cell voltage monitor (not shown).

The cleaning valves 124, 125 will be explained later.

<Cathode System>

The cathode system is provided with the compressor (the oxidizing gas supplying unit) 131, the dilution box 132, a silencer (a second dilution unit)133, and a flow rate sensor 134.

When the compressor 131 is operated in accordance with commands from the ECU 150, the compressor 131 sucks the air containing oxygen and presses the air toward the cathode flow path 112 via a pipe 131a. Also, the compressor 131 serves as the dilution gas flowing unit for flowing the cathode exhaust gas (the dilution gas) which dilutes the hydrogen in a below described first dilution unit D1.

The pipe 131a is connected to the silencer 133 (the second dilution unit) via a pipe 131b, and a part of the air exhausted from the compressor 131 is always supplied through the pipe 131b. In this way, at the time of cleaning of the hydrogen sensor 10A, the air (the dilution gas) from the pipe 131b dilutes the hydrogen from the hydrogen sensor 10A in the silencer 133. Therefore, the high concentration hydrogen for cleaning can be supplied to the hydrogen sensor 10A at the time of cleaning, and a temperature of a below described detection element 21 (see FIG. 4) can be much raised by the combustion heat of the hydrogen. Accordingly, the standby temperature of the detection element 21 can be lowered.

In addition, the pipe 131b may be provided with an normal closed-type solenoid valve (a flow rate adjusting device) which is opened at the time of cleaning of the hydrogen sensor 10A.

The cathode exhaust gas (the dilution gas) exhausted from the cathode flow path 112 is exhausted to an external (an outside) of the vehicle through the pipe 132a, the dilution box 132, the pipe 132b, the silencer 133, and the pipe 133a (a tailpipe).

The dilution box 132 mixes the anode exhaust gas from the opened purge valve 123 and the cathode exhaust gas so as to dilute the hydrogen contained in the anode exhaust gas, and includes a space for dilution for mixing (diluting). Therefore, at a predetermined time after the purge valve 123 was opened, the concentration of the hydrogen contained in the cathode exhaust gas (the dilution gas) from the dilution box 132 is raised a little (see FIG. 12).

<Silencer>

The silencer 133 reduces a noise which is caused by the compressor 131 and propagates through the air (containing the cathode exhaust gas) flowing through the cathode system, and includes a silence space (a chamber).

Here, the silencer 133 is placed at the downstream side of the hydrogen sensor 10A, and includes the silence space. Therefore, the silencer 133 serves as a second dilution unit for diluting the hydrogen from the hydrogen sensor 10A. In this way, at the time of cleaning of the hydrogen sensor 10A, the high-concentration hydrogen can be supplied to the detection element 21 (see FIG. 4) so as to increase the temperature rise by the combustion of the hydrogen. As a result, an amount of electricity supplied to the detection element 21 can be reduced.

The flow rate sensor 134 is attached to the pipe 131a, detects a flow rate of the air supplied to the cathode flow path 112, and outputs the flow rate to the ECU 150.

Figure 3:
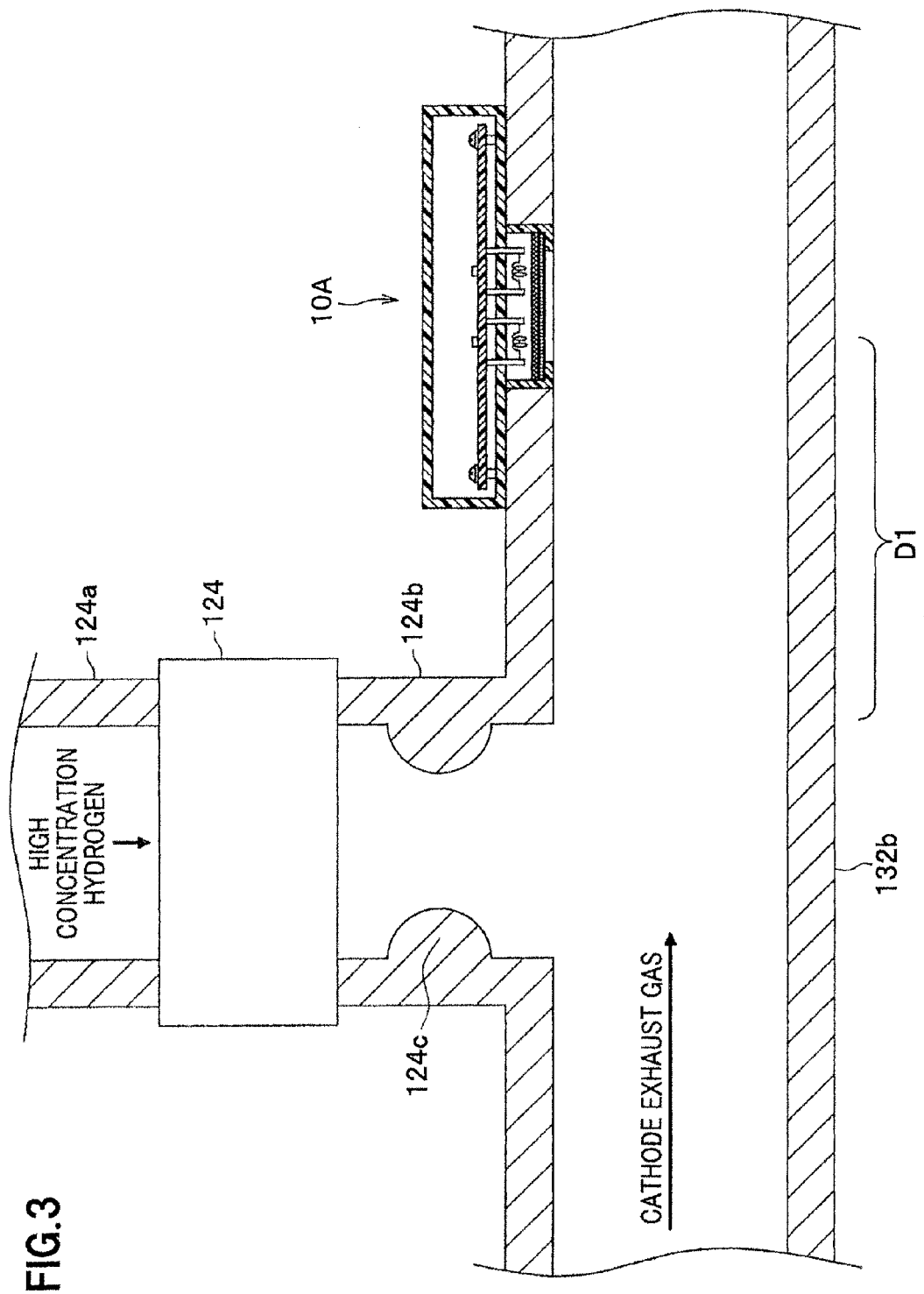
FIG. 3 is a side sectional view around a hydrogen sensor according to the embodiment.

Here, a flow rate of the air supplied to the cathode flow path 112 is proportional to that of the cathode exhaust gas (the dilution gas) from the cathode flow path 112 to a below described first dilution unit D1 (see FIG. 3). Therefore, the ECU 150 estimates (calculates) the flow rate of the cathode exhaust gas supplied to the first dilution unit D1 based on that of the air exhausted from the flow rate sensor 134.

<Hydrogen Sensor>

Figure 4:
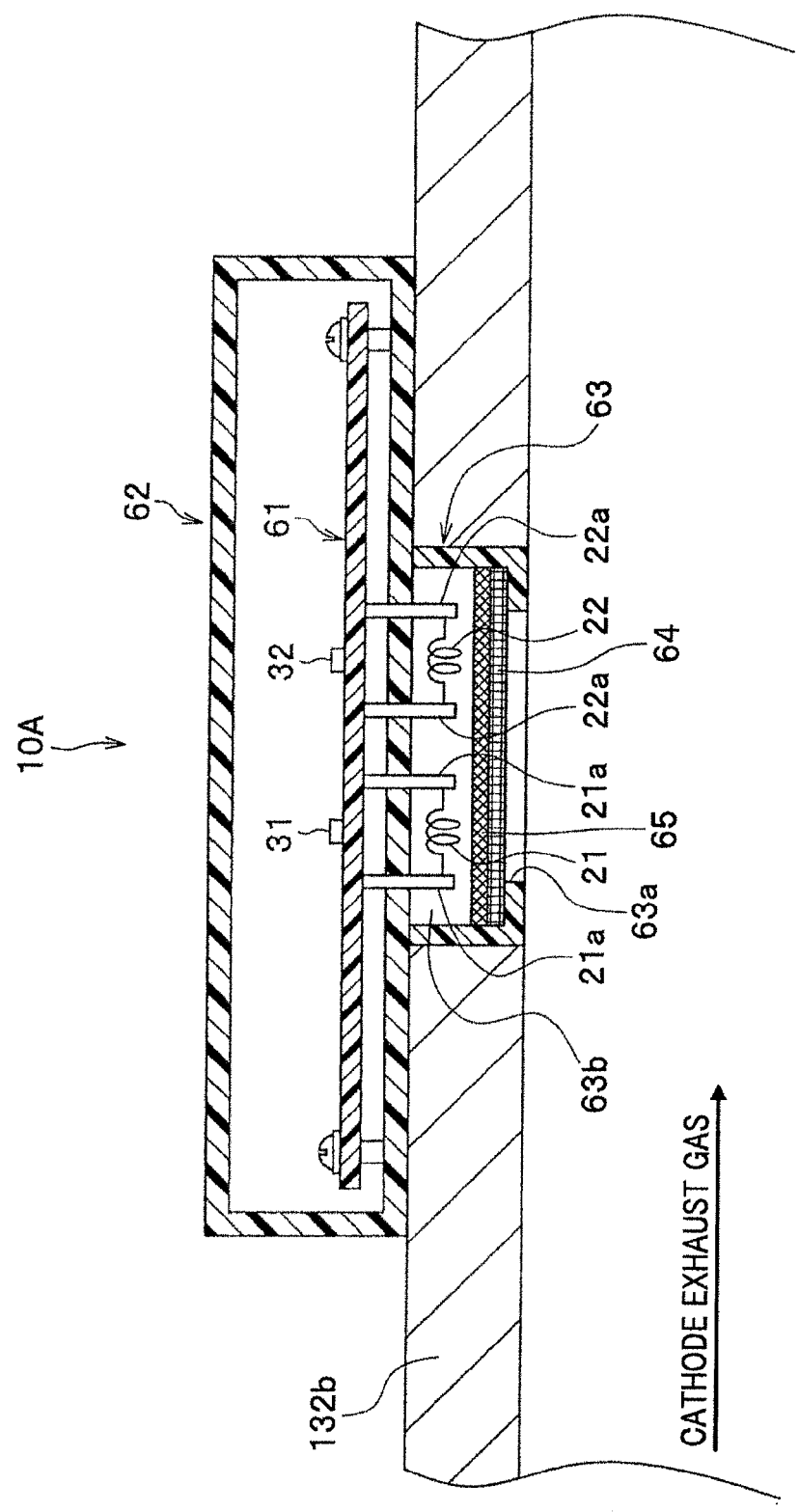
FIG. 4 is a side sectional view of a hydrogen sensor according to the embodiment.

Next, with reference to FIGS. 3-5, a structure of the hydrogen sensor 10A will be explained. In addition, since structures of the hydrogen sensors 10B-10D are the same as that of the hydrogen sensor 10A, the explanation will be omitted.

The hydrogen sensor 10A is a catalytic combustion type sensor for detecting the concentration of the hydrogen contained in a gas flowing through the pipe 132b, and is provided with a bridge circuit B, a control circuit 51, and a voltage generation circuit 52. A part of the bridge circuit B, the control circuit 51, and the voltage generation circuit 52 are composed of a circuit pattern formed on a below described substrate 61 and electronic components provided thereon.

Also, the hydrogen sensor 10A is provided with the substrate 61, a slim line casing 62 for housing the substrate 61, and a cylindrical housing 63 extending vertically downward from a bottom of the casing 62.

The casing 62 is attached to an upper wall of the pipe 132b via bolts (not shown).

The housing 63 is inserted into a through hole formed in the upper wall of the pipe 132b. Also, a gas containing the hydrogen and the silicon compound is interchanged between the pipe 132b and a gas detection chamber 63b in the housing 63 via a gas gateway 63a formed through the bottom wall of the housing 63.

A water-repellent filter 64 and an explosion proof filter 65 are provided so as to cover the gas gateway 63a. The water-repellent filter 64 allows the gas (the hydrogen) to pass but does not allows a liquid (a water drop) to pass, and are made of a tetrafluoroethylene membrane, etc. The explosion proof filter 65 ensures an explosion-proof character, and is made of a metal mesh or a porous body, etc. In addition, an adsorption filter having an activated carbon for absorbing the silicon compound, and a heater for vaporizing and removing condensation in the gas detection chamber 63b may be provided.

<Hydrogen Sensor—Bridge Circuit>

The bridge circuit B is composed of a first side 20 and a second side 30, and the first side 20 and the second side 30 are connected to the voltage generation circuit 52 in parallel.

The first side 20 is provided with a detection element 21 and a compensation element (a temperature compensation element) 22, and the detection element 21 is connected to the compensation element 22 in series.

The detection element 21 is fixed to metal stays 21a which extend vertically downward from the substrate 61 and are part of the first side 20, is placed in the gas detection chamber 63b, and is exposed in the gas detection chamber 63b. Likewise, the compensation element 22 is fixed to stays 22a, is placed in the gas detection chamber 63b, and is exposed in the gas detection chamber 63b.

Therefore, a resistor value $R_{21}$ of the detection element 21 and a resistor value $R_{22}$ of the compensation element 22 are varied based on a temperature (an ambient temperature, or an atmospheric temperature) in the gas detection chamber 63b.

The detection element 21 is made of a catalytic metal such as a platinum (Pt) or a platinum-alloy, etc. which causes a catalytic combustion of the hydrogen, and is not provide with a supported catalyst carrier (a catalyst layer) such as the platinum (Pt), etc. around itself. The detection element 21 according to the embodiment is made by forming a wire rod made of the catalytic metal into a coil shape, and its surface is smooth. Also, the surface forms a catalytic metal surface, and the hydrogen directly contacts the smooth catalytic metal surface (the surface of the detection element 21). In addition, since the detection element 21 is coil-shaped, the combustion heat of the hydrogen is not easily radiated and the temperature of the detection element 21 is raised easily. Also, other than the platinum (Pt), a palladium (Pd), a rhodium (Rh), an iron (Fe), a cobalt (Co), a nickel (Ni), and alloys thereof may be used as the catalytic metal.

In this way, the detection element 21 has a catalytic activity, and allows to proceed a catalytic combustion reaction (an oxidation-reduction reaction) between the hydrogen directly contacting the detection element 21 and the oxygen. Also, when the catalytic combustion reaction of the hydrogen occurs, the temperature of the detection element 21 is raised by the combustion heat.

Therefore, the temperature of the detection element 21, and the resistor value $R_{21}$ are varied based on the temperature of the gas detection chamber 63b and the combustion heat of the hydrogen.

The compensation element 22 is made by coating the surface of the coil shaped wire rod made of the catalytic metal with an inactive layer which is inactive to the hydrogen. The inactive layer is formed by a nonmetal such as an alumina ($Al_2O_3$) or silica ($SiO_2$), etc., or a metal such as a gold (Au), etc. which does not react with the hydrogen. In this way, if the hydrogen contacts the compensation element 22, the hydrogen does not react with the catalytic combustion reaction and the combustion heat is not generated.

Therefore, the temperature of the compensation element 22 and the resistor value $R_{22}$ are varied only based on the temperature (the ambient temperature, or the atmospheric temperature) in the gas detection chamber 63b.

The second side 30 is provided with a first resistor 31 (resistor value $R_{31}$) and a second resistor 32 (resistor value $R_{32}$) and is made by connecting the first resistor 31 to the second resistor 32 in series. The first resistor 31 and the second resistor 32 are provided on the substrate 61. In addition, the resistor value $R_{31}$ of the first resistor 31 and the resistor value $R_{32}$ of the second resistor 32 are known and fixed values.

Both ends of the first side 20 and both ends of the second side 30 are connected to an input terminal J1 and an input terminal J2 respectively. The input terminal J1 and the input terminal J2 are connected to the voltage generation circuit 52, and a voltage $V_{IN}$ generated by the voltage generation circuit 52 is applied to the input terminals J1 and J2 (the bridge circuit B). Also, when the voltage $V_{IN}$ generated by the voltage generation circuit 52 is applied, the detection element 21 is energized and the temperature of the detection element 21 is raised.

That is, in this embodiment, the heating unit (the power supplying unit) for energizing and heating the detection element 21 is provided with the voltage generation circuit 52 and a below described external power supply 70.

In the first side 20, a first middle point between the detection element 21 and the compensation element 22 serves as an output terminal J3. In the second side 30, a second middle point between the first resistor 31 and the second resistor 32 serves as an output terminal J4. The output terminal J3 and the output terminal J4 are connected to the control circuit 51, and an voltage $V_{OUT}$ (output) of the bridge circuit B is output to the control circuit 51 via the output terminals J3 and J4.

Also, when the resistor value $R_{21}$ (the detected value) of the detection element 21 is varied by the combustion heat of the hydrogen contacting the detection element 21 and the resistor value $R_{21}$ of the detection element 21 becomes higher than the resistor value $R_{22}$ of the compensation element 22, an electric potential of the output terminal J3 becomes than that of the output terminal J4, a voltage $V_{OUT}$ corresponding to the hydrogen concentration is output to the control circuit 51, and the hydrogen concentration is detected.

In addition, when the hydrogen does not contact the detection element 21 and the combustion heat of the hydrogen is not generated, the resistor value $R_{21}$ of the detection element 21 is equal to the resistor value $R_{22}$ of the compensation element 22, the electric potential of the output terminal J3 is equal to that of the output terminal J4, and the voltage $V_{OUT}$ becomes 0.

<Hydrogen Sensor—Control Circuit, Etc.>

The control circuit 51 comprises a CPU, a ROM, a RAM, a variety of interfaces, and an electronic circuit, etc. Also, the control circuit 51 appropriately controls the hydrogen sensor 10A in accordance with commands from the ECU 150 and a program stored in the control circuit 51.

That is, the control circuit 51 operates the voltage generation circuit 52 in accordance with commands from the ECU 150, calculates the hydrogen concentration based on the voltage $V_{OUT}$ from the bridge circuit B, and outputs a signal corresponding to the hydrogen concentration to the ECU 150.

However, the present invention is not limited to the above structure. For example, the ECU 150 may directly control the voltage generation circuit 52, and the voltage $V_{OUT}$ of the bridge circuit B may be output to the ECU 150 directly.

The voltage generation circuit 52 is provided with a DC-DC converter, etc., and is connected to the external power supply 70 (e.g., a 12 volt battery). Also, the voltage generation circuit 52 is operated in accordance with commands from the control circuit 51, and applies a predetermined voltage to the bridge circuit B.

<Hydrogen Sensor Adhering Mass of Silicon Compound>

Figure 6:
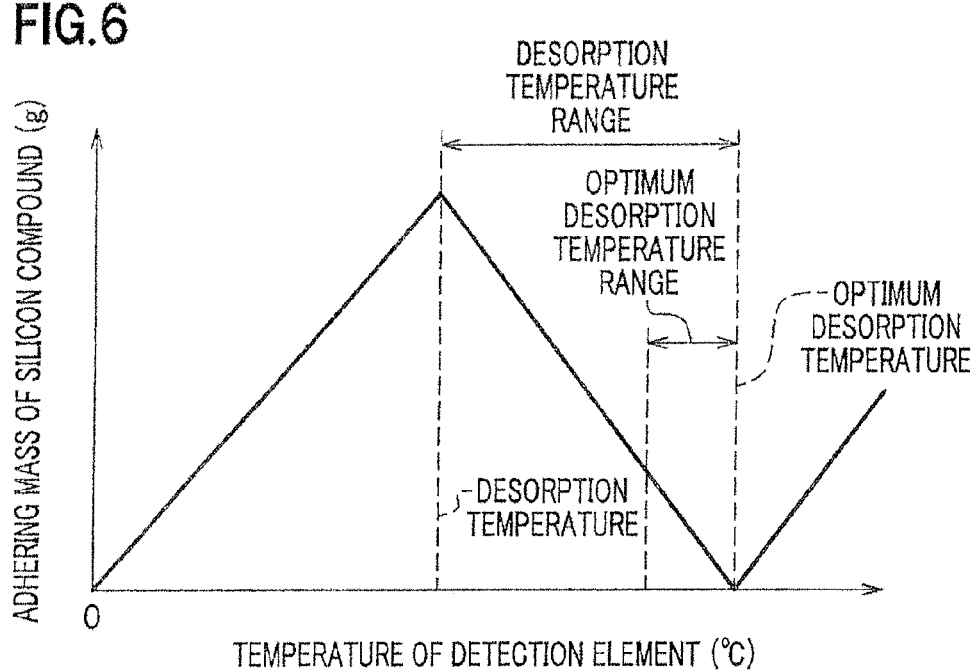
FIG. 6 is a graph showing a relation between a temperature of a detection element and an adhering mass of a silicon compound.

Here, as shown in FIG. 6, inventors of the present invention has known that as the temperature of the detection element 21 made of the catalytic metal such as the platinum, etc., is raised in a silicon atmosphere, the adhering mass (silicon poisoning) (g) of the silicon compound to the detection element 21 is increased, but within a predetermined desorption temperature range, the adhering mass of the silicon compound is decreased.

The above situation arises since the silicon compound adhering to the detection element 21 is desorbed from the detection element 21 within the desorption temperature. That is, within the desorption temperature range, a desorption rate of the silicon compound is smaller than a adherence rate of the silicon compound, but is approximately the same in the order of magnitude. Also, the desorption rate is approximately equal to the adherence rate at an optimum desorption temperature. and the adherence rate is greater than the desorption rate when the temperature is higher than the optimum desorption temperature.

Also, within the range of the desorption temperature, as the temperature of the detection element 21 is raised, the adhering mass (g) of the silicon compound is decreased. Also, at the optimum desorption temperature, the adhering mass is minimized. That is, in order to recover the hydrogen detection sensitivity of the hydrogen sensor 10A, the temperature of the detection element 21 is raised to the range of the desorption temperature, preferably to the optimum desorption temperature range including the optimum desorption temperature (e.g., "the optimum desorption temperature −10 Celsius degree"—"the optimum desorption temperature").

Figure 7:
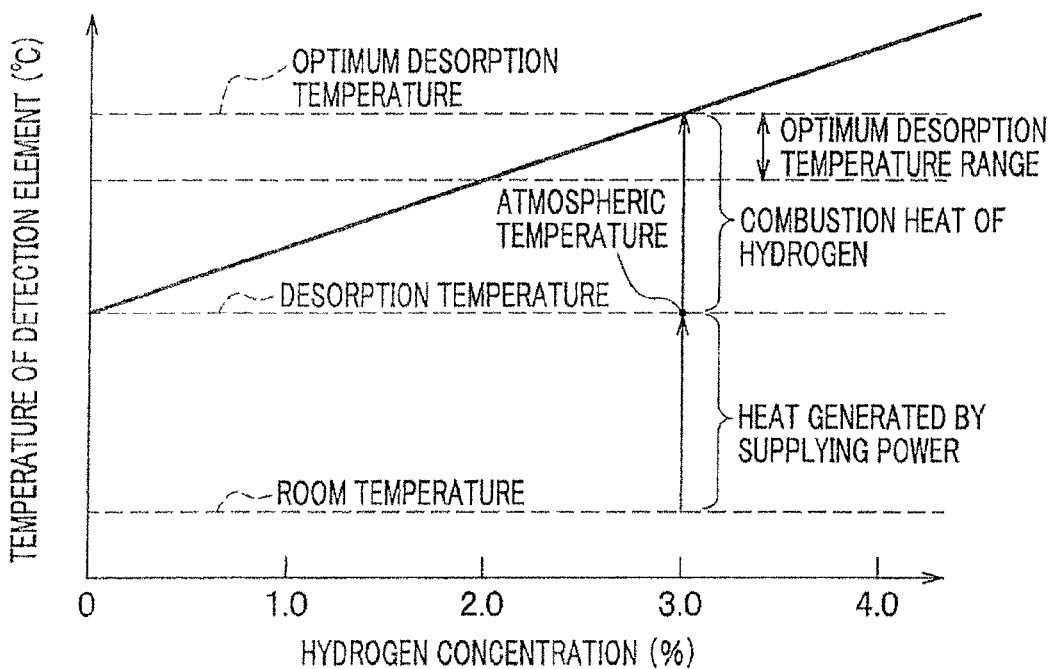
FIG. 7 is a graph showing a relation between a hydrogen concentration and the temperature of the detection element.

Based on the above, in this embodiment, in order to raise the temperature of the detection element 21 to the optimum desorption temperature range at the time of cleaning of the hydrogen sensor 10A, the heat generated by supplying power to the detection element 21 and the combustion heat generated by the contact between the detection element 21 and the hydrogen are used (see FIG. 7).

That is, as shown in FIG. 7, at the time of cleaning (when the sensitivity recovery process is executed) and at the time of non-cleaning (when the sensitivity recovery process is not executed, on standby), in consideration of the concentration of the hydrogen from the first dilution unit D1, the temperature of the detection element 21 is raised from a room temperature to a standby temperature by supplying power to the detection element 21, and is further raised to the optimum desorption temperature range by the combustion heat at the time of cleaning. Also, in this embodiment, the standby temperature is set to a temperature obtained by subtracting the temperature rise caused by the combustion of the hydrogen from the optimum desorption temperature.

<Cleaning Valve>

Next, with reference to FIGS. 2, 3, and 8, a structure around the cleaning valves 124 and 125 will be explained.

<Cleaning Valve For Hydrogen Sensor 10A>

As described later, the pipe 121a which is downstream of the pressure reducing valve is connected to the pipe 132b which is upstream of the hydrogen sensor 10A via the pipe 124a, the cleaning valve 124, and a pipe 124b. Also, at the time of cleaning of the hydrogen sensor 10A (when the sensitivity recovery process is executed), when the cleaning valve 124 is opened in accordance with commands from the ECU 150, the high-concentration hydrogen flows from the hydrogen tank 121 to the hydrogen sensor 10A through the pipe 121a, the pipe 124a, and the pipe 124b.

That is, in this embodiment, the hydrogen guiding pipe for guiding the hydrogen from the hydrogen tank 121 to the detection element 21 of the hydrogen sensor 10A is provided with the pipe 124a and the pipe 124b. Also, the hydrogen guiding pipe is provided with the cleaning valve 124 (the flow rate adjusting device).

The pipe 124b is provided with an orifice 124c which reduces the flow rate of the hydrogen flowing from the pipe 124b into the pipe 132b. In this way, by opening/closing the cleaning valve 124, the concentration of the hydrogen supplied to the hydrogen sensor 10A can easily be controlled after the hydrogen flows into the pipe 123b and is diluted by a below described first dilution unit D1.

However, the orifice 124c is not limited to be downstream of the cleaning valve 124, and may be upstream of the cleaning valve 124. Also, the orifice 124c may be omitted.

Also, the pipe 124a joins the pipe 132b (the cathode exhaust gas flow path) which is upstream of the hydrogen sensor 10A. Also, the pipe 132b (the cathode exhaust gas flow path) between a confluence of the pipe 124b and the hydrogen sensor 10A serves as the first dilution unit D1 for diluting the hydrogen supplied from the cleaning valve 124 with the cathode exhaust gas (the dilution gas) (see FIG. 3). In addition, the first dilution unit D1 is placed between the cleaning valve 124 and the hydrogen sensor 10A.

The cleaning valve 124 is an normal closed-type solenoid valve (a valve unit) driven by a solenoid. For example, the cleaning valve 124 is composed of a gate valve, and keeps a predetermined open state (an opening degree) while receiving a valve-opening command from the ECU 150.

Also, for example, the ECU 150 performs a PWM control of the open time/close time of the cleaning valve 124 so that the flow rate of the hydrogen (the high-concentration hydrogen) supplied to the pipe 132b (the first dilution unit D1) through the cleaning valve 124 can be controlled easily. As a result, the concentration of the hydrogen supplied to the detection element 21 of the hydrogen sensor 10A can be controlled.

<Cleaning Valve for Hydrogen Sensor 10B (10C, 10D)>

The pipe 125a, the normal closed-type cleaning valve 125, and a pipe 125b are sequentially connected to a midway of the pipe 124a. The downstream end of the pipe 125b is placed so that the hydrogen is supplied from the pipe 125b to the hydrogen sensor 10B (10C, 10D). That is, the pipe 125a, a cleaning valve 125, and the pipe 125b are provided for each of the hydrogen sensors 10B-10D, but are omitted in FIG. 2.

Also, at the time of cleaning the hydrogen sensor 10B (10C, 10D) (when the sensitivity recovery process is executed), when the cleaning valve 125 is opened in accordance with commands from the ECU 150, the high-concentration hydrogen flows from the hydrogen tank 121 to the hydrogen sensor 10B (10C, 10D) through the pipe 121a, the pipe 124a, the pipe 125a, and the pipe 125b.

That is, in this embodiment, the hydrogen guiding pipe for guiding the hydrogen from the hydrogen tank 121 to the detection element 21 of the hydrogen sensor 10B (10C, 10D) is provided with a part of the pipe 124a, the pipe 125a, and the pipe 125b. Also, the hydrogen guiding pipe is provided with the cleaning valve 125 (the flow rate adjusting device).

The pipe 125b is provided with an orifice 124c which reduces the flow rate of the hydrogen flowing from the pipe 125b to the below described first dilution unit D2 (see FIG. 8).

In this way, by opening/closing the cleaning valve 125, the concentration of the hydrogen supplied to the hydrogen sensor 10B can easily be controlled after the hydrogen is diluted by the first dilution unit D2.

However, the orifice 124c is not limited to be downstream of the cleaning valve 125, and may be upstream of the cleaning valve 125. Also, the orifice 124c may be omitted.

Figure 8:
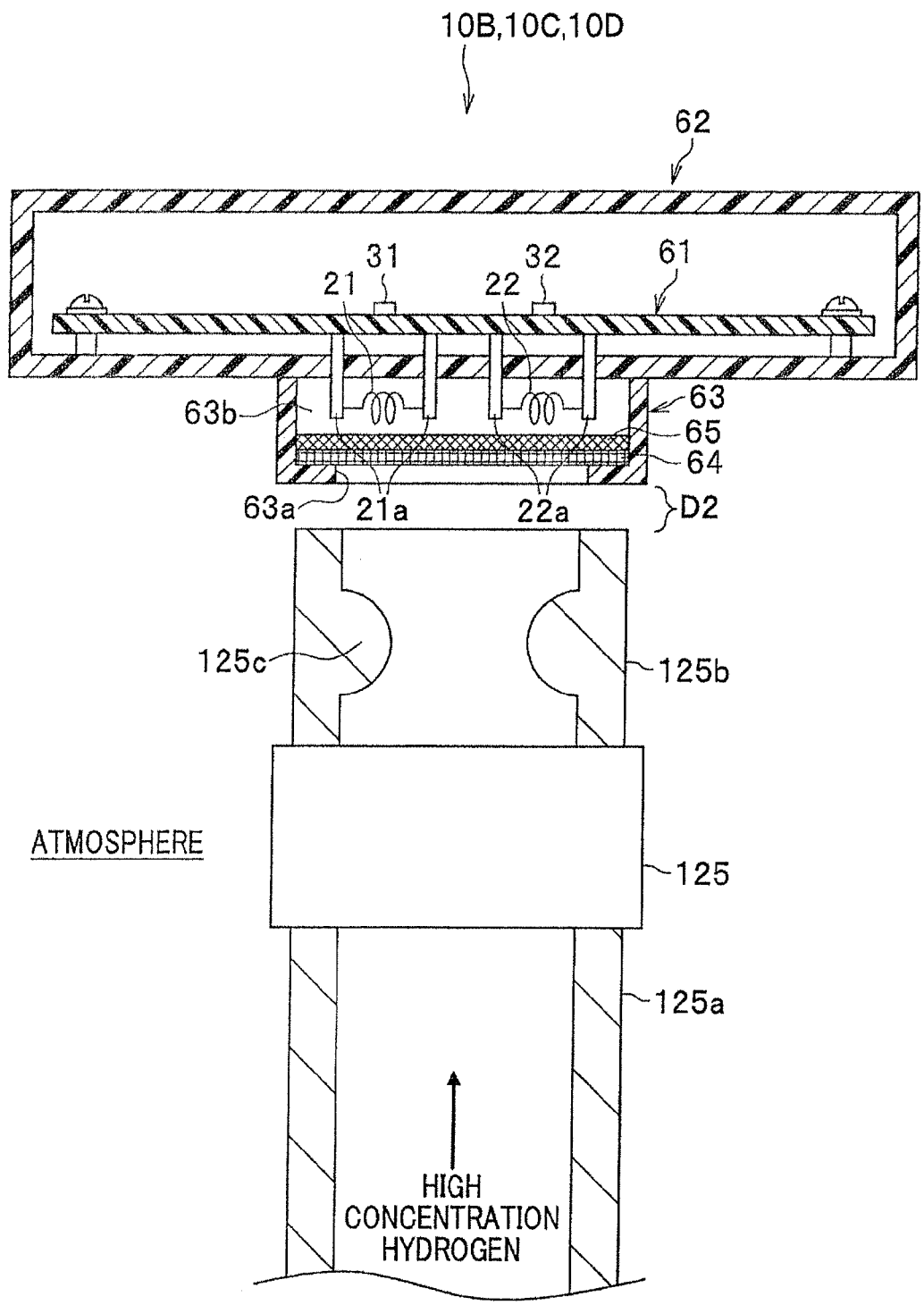
FIG. 8 is a side sectional view around a hydrogen sensor according to the embodiment.

As shown in FIG. 8, the downstream end of the pipe 125b and the hydrogen sensor 10B are placed at a predetermined space determined by an experiment, etc. in advance, and are composed of the first dilution unit D2 (the space for dilution) opened to the atmosphere. That is, the first dilution unit D2 is placed between the cleaning valve 125 and the hydrogen sensor 10B (10C, 10D). Also, the first dilution unit D2 makes the hydrogen from the pipe 125b self-diffusion and dilutes the hydrogen with the air (the dilution gas).

Like the cleaning valve 124, the cleaning valve 125 is the normal closed-type solenoid valve (the valve unit) driven by the solenoid. For example, the cleaning valve 125 is composed of a gate valve driven by the solenoid, and keeps a predetermined open state (an opening degree) while receiving a valve-opening command from the ECU 150.

Also, for example, the ECU 150 performs a PWM control of the open time/close time of the cleaning valve 125 so that the flow rate of the hydrogen (the high-concentration hydrogen) supplied to the first dilution unit D2 through the cleaning valve 125 can be controlled easily. As a result, the concentration of the hydrogen supplied to the detection element 21 of the hydrogen sensor 10B (10C, 10D) can be controlled.

In this case, when an atmospheric pressure (an atmospheric pressure) decreases, an atmospheric pressure sensor for detecting the atmospheric pressure is provided since it becomes difficult to dilute the hydrogen with the air (the dilution gas) in the first dilution unit D2. When the fuel cell vehicle 200 travels on a high place, the open time of the cleaning valve 125 may be shortened as the atmospheric pressure decreases.

That is, in this embodiment, the cleaning can be executed by only the fuel cell vehicle 200 since the hydrogen tank 121 can supply not only the hydrogen (the fuel gas) to the fuel cell stack 110 but also the hydrogen for cleaning to the hydrogen sensors 10A-10D.

<IG>

An IG 141 is a starting switch of the fuel cell vehicle 200 (the fuel cell system 100, the hydrogen detection system 1), and is placed around a driver's seat. Also, the IG 141 outputs an ON signal/OFF signal to the ECU 150.

<ECU>

The ECU 150 controls the fuel cell vehicle 200 (the fuel cell system 100, the hydrogen detection system 1), and comprises a CPU, a ROM, a RAM, a variety of interfaces, and an electronic circuit, etc. Also, the ECU 150 performs a variety of functions in accordance with a program stored in the control circuit 51 and controls a variety of apparatus, A motion of the ECU 150 will be explained later.

<<Motion of Fuel Cell Vehicle>>

Next, a motion of the fuel cell vehicle 200 will be explained.

<Activation Mode>

First, with reference to FIG. 9, a motion of the fuel cell vehicle 200 in an activation mode at the time of activation (starting) will be explained.

Figure 9:
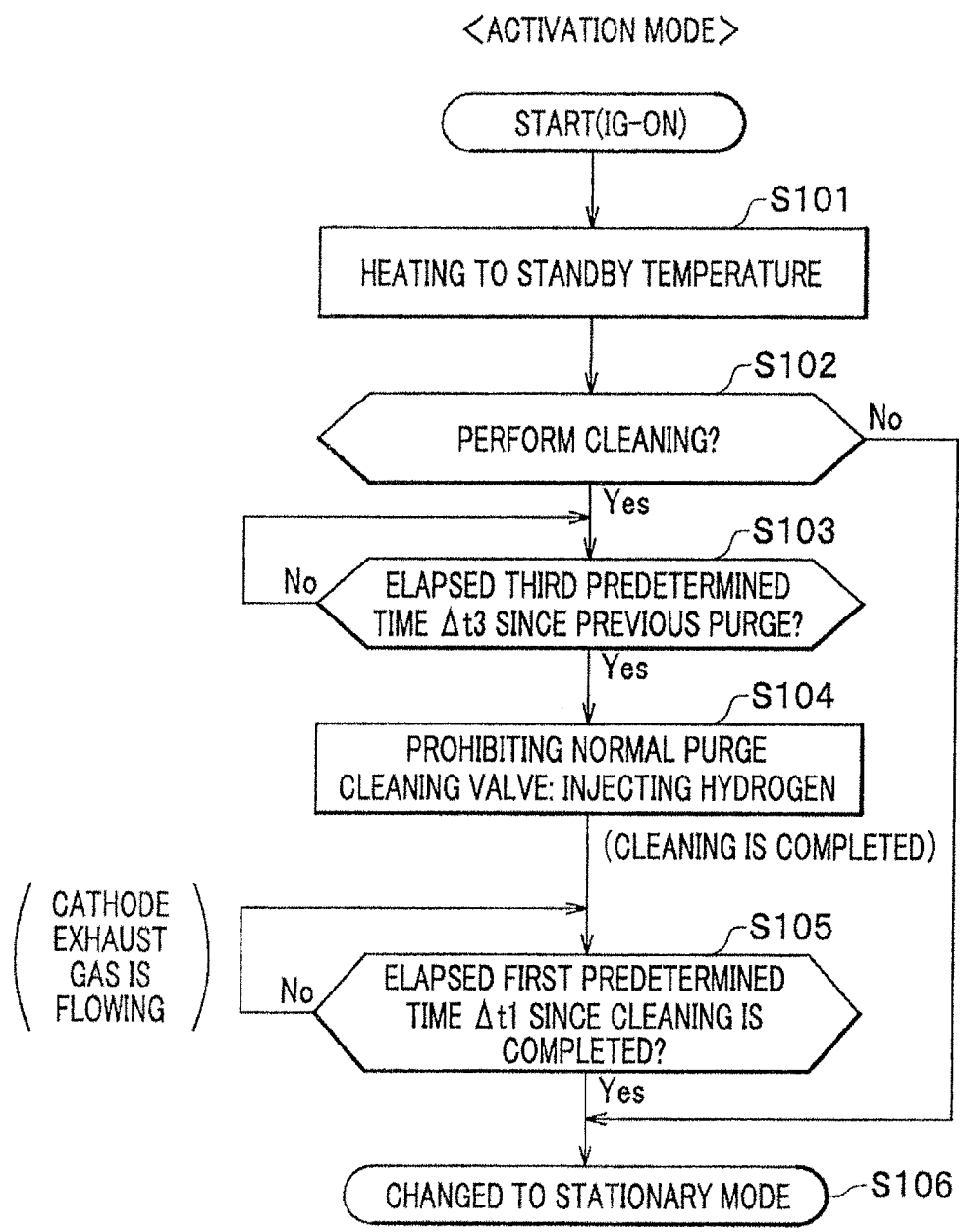
FIG. 9 is a flowchart showing a motion of the fuel cell vehicle according to the embodiment in a activation mode.

In addition, when the IG 141 is turned ON, the ECU 150 detects an ON signal and stars a process shown in FIG. 9. Also, although a motion of the hydrogen sensor 10A will be explained, motions of the hydrogen sensors 10B-10D will be omitted since those of the hydrogen sensors 10B-10D is the same as that of the hydrogen sensor 10A.

Further, the ECU 150 executes a process of a power generation by the fuel cell stack 110 in parallel with a below described process by the hydrogen sensor 10A.

That is, the ECU 150 commands a shutdown valve (not shown) provided at the pipe 121a to open so that the hydrogen is supplied to the anode flow path 111, the purge valve 123 is opened intermittently, and the hydrogen concentration is raised in the anode flow path 111. In parallel, the ECU 150 commands the compressor 131 to operate so as to supply the air (the oxygen) to the cathode flow path 112. As a result, an OCV (Open Circuit Voltage) of the fuel cell stack 110 is raised, and the fuel cell stack 110 is moved closer to a power generating condition.

Also, if the OCV becomes equal to or greater than a predetermined OCV at which power generation can be started, the ECU 150 controls a power generation controller (not shown) connected to an output terminal of the fuel cell stack 110, extracts a current from the fuel cell stack 110, causes the fuel cell stack 110 to start power generation, and supplies the generated electric power to an outer load (a motor for traveling, etc.). In this case, the larger a required power generation quantity (an accelerator opening degree, etc.), the higher a rotation speed of the compressor 131, and the electric power generated by the fuel cell stack 110.

Hereinafter, a process regarding the hydrogen sensor 10A will be explained.

In step S101, the ECU 150 heats the detection element 21 of the hydrogen sensor 10A and the compensation element 22 to the standby temperature, In this embodiment, the standby temperature is set to a temperature obtained by subtracting a temperature rise caused by a combustion heat of the hydrogen at the time of cleaning from a temperature within the optimum desorption temperature range which is equal to or greater than the desorption temperature at the time of cleaning of the hydrogen sensor 10A (when the sensitivity recovery process is executed) (see FIGS. 6 and 7).

For example, the temperature rise caused by the combustion heat of the hydrogen at the time of cleaning is a predetermined temperature rise obtained by an experiment in advance.

In addition, the temperature rise caused by the combustion heat of the hydrogen at the time of cleaning may be calculated based on the concentration of the hydrogen supplied from the first dilution unit D1 to the detection element 21 (the hydrogen sensor 10A) at the time of cleaning. That is, the standby temperature can be set corresponding to the concentration of the hydrogen diluted by the first dilution unit D1, and the standby temperature is achieved by supplying power to the detection element 21 to heat it. In this case, the concentration of the hydrogen supplied from the first dilution unit D1 to the detection element 21 at the time of cleaning is calculated based on the open time of the cleaning valve 124 and the flow rate of the cathode exhaust gas.

Figure 5:
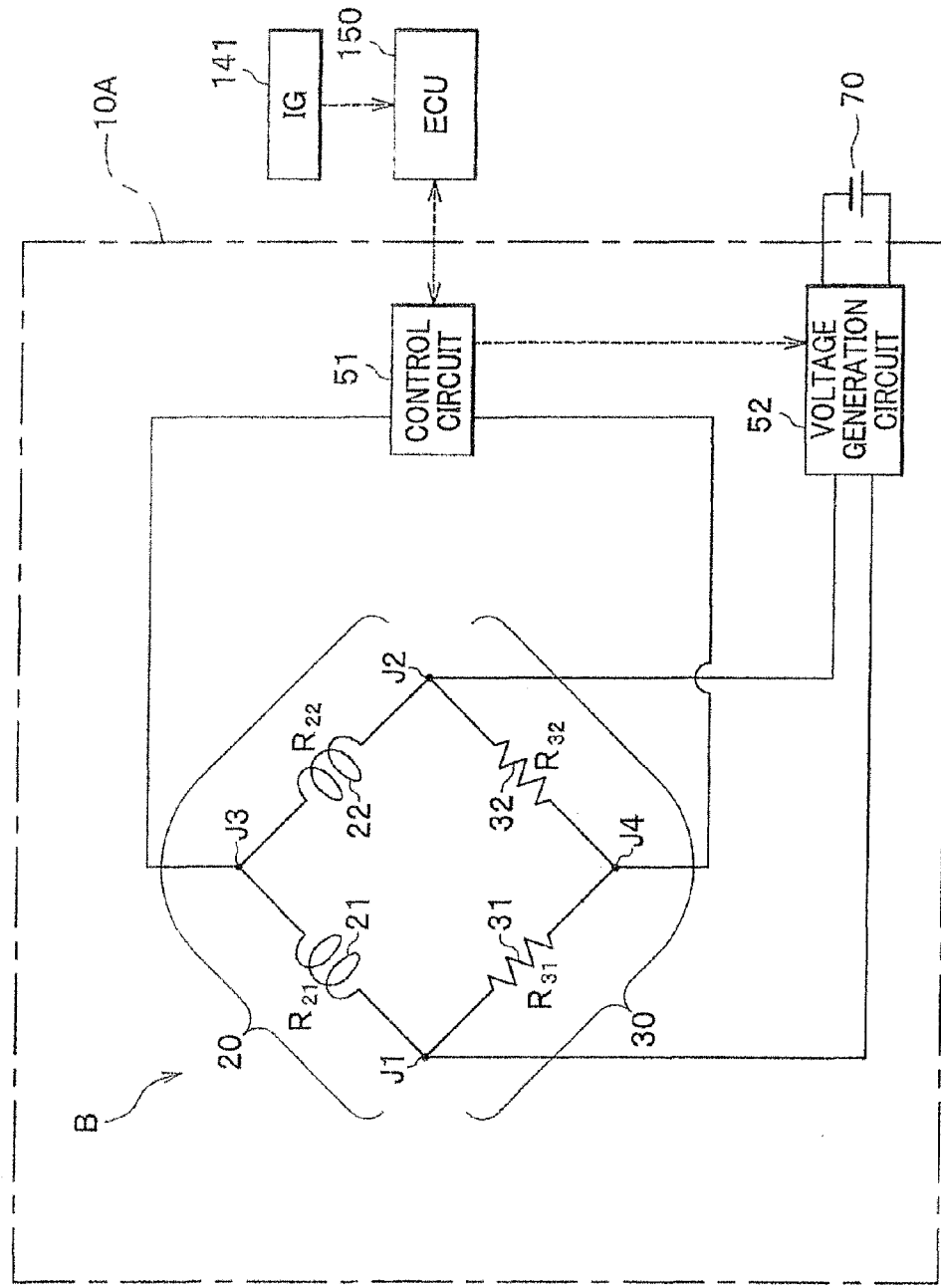
FIG. 5 is a circuit diagram of the hydrogen sensor according to the embodiment.

Concretely, the ECU 150 outputs a standby temperature heating command corresponding to the standby temperature to the voltage generation circuit 52 via the control circuit 51 (see FIG. 5). Also, the voltage generation circuit 52 converts the electric power supplied from the external power supply 70 to a corresponding to the standby temperature heating command (the standby temperature) and supplies the standby voltage to the bridge circuit B. In this way, temperatures of the detection element 21 and the compensation element 22 are raised to the standby temperature by supplying power.

In step S102, the ECU 150 determines whether the cleaning of the detection element 21 (the hydrogen sensor 10A) is needed to be performed or not (the sensitivity recovery is required or not).

Concretely, if the adhering mass of the silicon compound adhering to the detection element 21 is equal to or greater than a predetermined adhering mass at which the cleaning is determined to be performed for recovering the sensitivity, the cleaning is determined to be performed.

Here, the adhering mass of the silicon compound adhering to the detection element 21 is proportional to used hours of the hydrogen sensor 10A, power generation hours (a integrated power generation quantity) of the fuel cell stack 110, and an operation time (an ON time of the IG 141) of the fuel cell system 100 (the fuel cell vehicle 200), etc. Therefore, (1) if the integrated used hours of the hydrogen sensor 10A from the previous cleaning to the present is equal to or greater than a predetermined integrated used hours, (2) if an integrated power generation hours (an integrated power generation quantity) from the previous cleaning of the fuel cell stack 110 to the present is equal to or greater than a predetermined integrated power generation hours (a predetermined integrated power generation quantity), and (3) an operation time of the fuel cell system 100 (the fuel cell vehicle 200) from the previous cleaning to the present is equal to or greater than a predetermined operation time, the cleaning is determined to be performed.

Here, inventors of the present invention has known that the adhering mass of the silicon tends to increase if the hydrogen sensor 10A is used in the atmosphere in a predetermined hydrogen concentration range. That is, there exists a hydrogen concentration range within which the silicon compound tends to adhere. For this reason, considering the time during which the hydrogen concentration detected by the hydrogen sensor 10A is within the predetermined hydrogen concentration range, the used hours, etc., may be revised based on the above fact.

If the cleaning is determined to be performed (S102: Yes), the process of the ECU 150 proceeds to step S103. On the other hand, if the cleaning is determined not to performed (S102: No), the process of the ECU 150 proceeds to step S106.

In step S103, the ECU 150 determines whether a third predetermined time $\Delta t3$ has elapsed since a previous purge (closing the purge valve 123).

Figure 12:
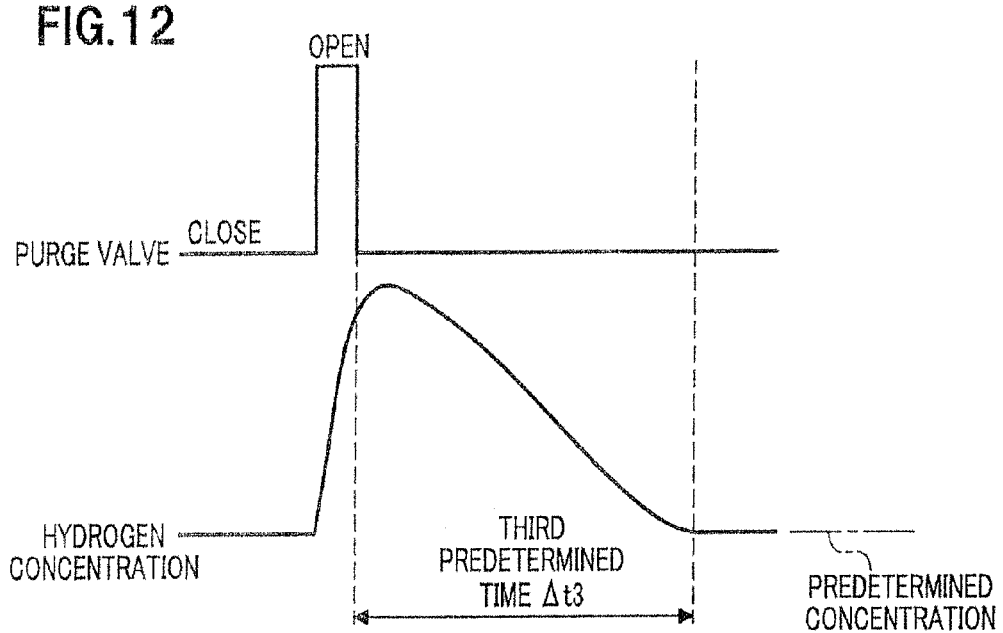
FIG. 12 is a timing diagram showing a relation between an open/close motion of a purge valve and a hydrogen concentration.

Here, as described above, the ECU 150 commands the purge valve 123 to open intermittently at the predetermined open time. Therefore, as shown in FIG. 12, the hydrogen concentration in the first dilution unit D1 (see FIG. 3) is raised linked to opening of the purge valve 123. The hydrogen is diluted with the cathode exhaust gas (the dilution gas) passing through the pipe 132*b* after the purge valve 123 is closed, and the hydrogen concentration is gradually decreased. Also, the third predetermined time $\Delta t3$ is set to a time during which the hydrogen concentration is decreased to the predetermined concentration in the first dilution unit D1 since the purge valve 123 is closed. The predetermined concentration is set so that the high-concentration hydrogen is appropriately diluted in the first dilution unit D1 so as to become the hydrogen having an appropriate concentration even if the cleaning valve 124 is opened and the high-concentration hydrogen is injected into the pipe 132*b* thereafter, and the temperature of the detection element 21 is changed within the optimum desorption temperature range by the combustion heat of the hydrogen having the appropriate concentration.

Therefore, when the open time of the purge valve 123 is varied, the third predetermined time $\Delta t3$ may be revised long as the open time of the purge valve 123 becomes long. Also, when the flow rate of the cathode exhaust gas is increased, the hydrogen becomes easy to be diluted and the hydrogen concentration falls rapidly. Therefore, third predetermined time $\Delta t3$ may be revised short as the flow rate of the cathode exhaust gas estimated from the air flow rate detected by the flow rate sensor 134 is increased.

If it is determined that the third predetermined time $\Delta t3$ has elapsed (S103: Yes), the process of the ECU 150 proceeds to step S104. On the other hand, if it is determined that the third predetermined time $\Delta t3$ has not elapsed (S103: No), the ECU 150 repeats a judgment in step S103.

In step S104, the ECU 150 prohibits a normal purge. That is, the ECU 150 prohibits opening of the purge valve 123, and keeps the purge valve 123 closed.

In parallel, in step S104, the ECU 150 opens the cleaning valve 124 at the open time. As a result, the high-concentration hydrogen is injected from the hydrogen tank 121 into the pipe 132*b* through the pipe 121*a*, the pipe 124*a*, and the pipe 124*b*. Then, the injected hydrogen is appropriately diluted with the cathode exhaust gas (the dilution gas) in the first dilution unit D1 and becomes the hydrogen having an appropriate concentration. Also, the hydrogen having an appropriate concentration is injected to the detection element 21 of the hydrogen sensor 10A, and the temperature of the detection element 21 is changed within the optimum desorption temperature range by the combustion heat of the hydrogen (see FIG. 7). In this way, the silicon compound adhering to the detection element 21 is desorbed from the detection element 21 (see FIG. 6), and the sensitivity of the detection element 21 (the hydrogen sensor 10A) is recovered. Also, cleaning is completed when the cleaning valve 124 is closed in accordance with commands from the ECU 150.

Here, although the open time at which the cleaning valve 124 is opened may be a fixed time determined by an experiment, etc. in advance, the open time may be revised long so that the hydrogen injected into the pipe 132*b* is increased as the flow rate of the cathode exhaust gas estimated from the air flow rate detected by the flow rate sensor 134 is increased.

In step S105, the ECU 150 determines whether a first predetermined time $\Delta t1$ has elapsed since the cleaning in step S104 is completed (the sensitivity recovery process is completed).

Figure 13:
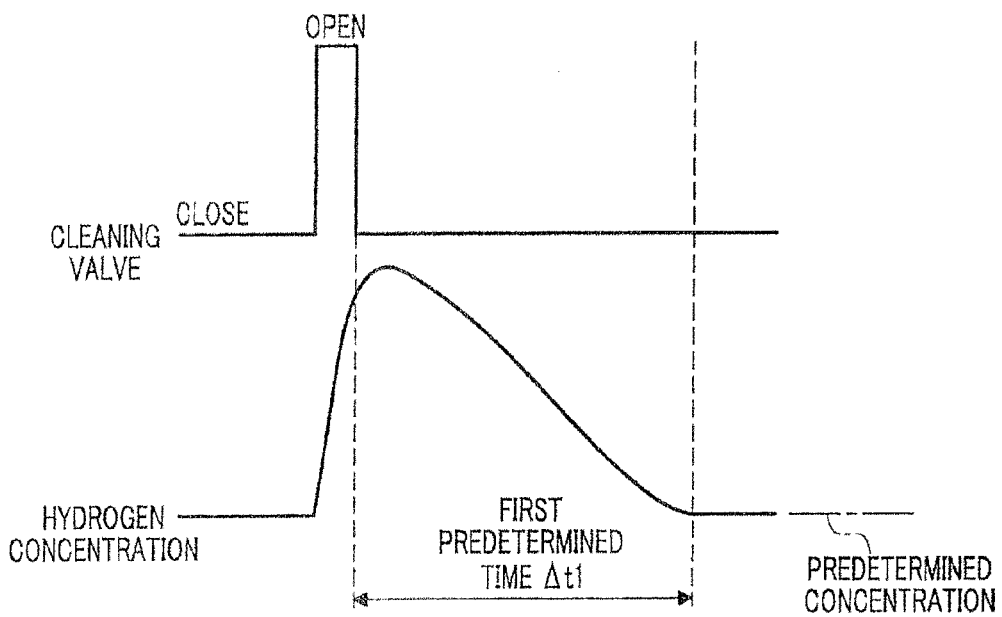
FIG. 13 is a timing diagram showing a relation between a open/close motion of a cleaning valve and a hydrogen concentration.

Here, as shown in FIG. 13, when the cleaning valve 124 is opened in step S104, the hydrogen concentration in the first dilution unit D1 (see FIG. 3) is raised. The hydrogen is diluted with the cathode exhaust gas (the dilution gas) passing through the pipe 132*b* after the cleaning valve 124 is closed, and the hydrogen concentration is gradually decreased. Also, the first predetermined time $\Delta t1$ is set to a time during which the hydrogen concentration is decreased to the predetermined concentration in the first dilution unit D1 since the cleaning valve 124 is closed. The predetermined concentration is set so that the high-concentration hydrogen is appropriately diluted in the first dilution unit D1 so as to become the hydrogen having an appropriate concentration even if the cleaning valve 124 is opened and the high-concentration hydrogen is injected into the pipe 132*b* thereafter, and the temperature of the detection element 21 is changed within the optimum desorption temperature range by the combustion heat of the hydrogen having the appropriate concentration.

If it is determined that the first predetermined time $\Delta t1$ has elapsed (S105: Yes), the process of the ECU 150 proceeds to step S106.

On the other hand, if it is determined that the first predetermined time $\Delta t1$ has not elapsed (S105: No), the ECU 150 repeats the judgment in step S105. If the judgment in step S105 is repeated (i.e., if the first predetermined time Δt1 has not elapsed since the cleaning valve 124 is closed), the cathode exhaust gas (the dilution gas) flows through the first dilution unit D1, the hydrogen concentration falls rapidly in the first dilution unit D1, and the next cleaning can be executed rapidly since the ECU 150 operates the compressor 131 (the dilution gas flowing unit).

Figure 10:
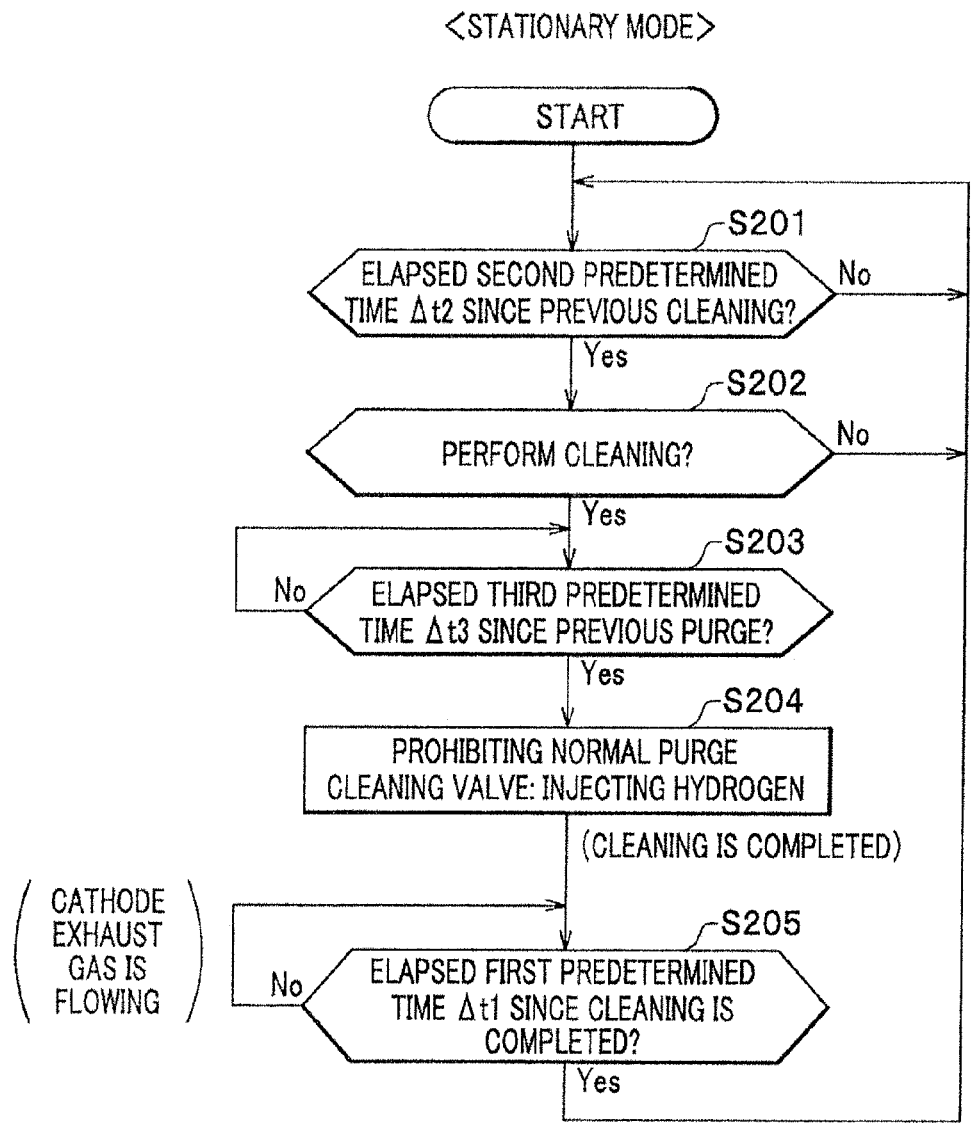
FIG. 10 is a flowchart showing a motion of the fuel cell vehicle according to the embodiment in a stationary mode.

In step S106, the ECU 150 completes the motion in the activation mode, and changes the mode to a stationary mode shown in FIG. 10.

<Stationary Mode>

Next, with reference to FIG. 10, a motion of the fuel cell vehicle 200 in a stationary mode will be explained.

In addition, the hydrogen and the air are supplied to the fuel cell stack 110, and the fuel cell stack 110 generates power corresponding to the required power generation quantity. Also, the purge valve 123 is opened intermittently in accordance with commands from the ECU 150.

In step S201, the ECU 150 determines whether a second predetermined time Δt2 has elapsed since the previous cleaning (S204).

In addition, If the cleaning is determined not to be performed (S202: No) when the second predetermined time Δt2 has elapsed (S201 Yes), the time at which the cleaning is determined not to be performed is used as a base time. Also, the second predetermined time Δt2 is set to be equal to or greater than the first predetermined time Δt1.

If it is determined that the second predetermined time Δt2 has elapsed (S201: Yes), the process of the ECU 150 proceeds to step S202. On the other hand, if it is determined that the second predetermined time Δt2 has not elapsed (S201: No), the ECU 150 repeats the judge in step S201.

In step S202, like step S102, the ECU 150 determines whether the cleaning of the detection element 21 (the hydrogen sensor 10A) is needed to be performed or not (whether the sensitivity recovery is required or not).

If it is determined that the cleaning is needed to be performed (S202: Yes), the process of the ECU 150 proceeds to step S203. On the other hand, if it is determined that the cleaning is not needed to be performed (S202: No), the process of the ECU 150 proceeds to step S201.

In step S203, like step S103, the ECU 150 determines whether the third predetermined time Δt3 has elapsed since the previous purge.

If it is determined that the third predetermined time Δt3 has elapsed (S203: Yes), the process of the ECU 150 proceeds to step S204. On the other hand, if it is determined that the third predetermined time Δt3 has not elapsed (S203: No), the ECU 150 repeats the judgment in step S203.

In step S204, like step S104, the ECU 150 prohibits the normal purge. That is, the ECU 150 prohibits opening the purge valve 123, and keeps the purge valve 123 closed, opens the cleaning valve 124 at the open time, and performs the cleaning of the hydrogen sensor 10A.

In step S205, like step S105, the ECU 150 determines whether the first predetermined time Δt1 has elapsed since the cleaning in step S204 is completed.

If it is determined that the first predetermined time Δt1 has elapsed (S205: Yes), the process of the ECU 150 proceeds to step S201.

On the other hand, if it is determined that the first predetermined time Δt1 has not elapsed (S205: No), the ECU 150 repeats the judgment in step S205. If the judgment in step S205 is repeated, the cathode exhaust gas (the dilution gas) flows through the first dilution unit D1, the hydrogen concentration falls rapidly in the first dilution unit D1, and the next cleaning can be executed rapidly since the ECU 150 operates the compressor 131 (the dilution gas flowing unit).

<Stopping Mode>

Next, with reference to FIG. 11, a motion of the fuel cell vehicle 200 in a stopping mode will be explained.

Figure 11:
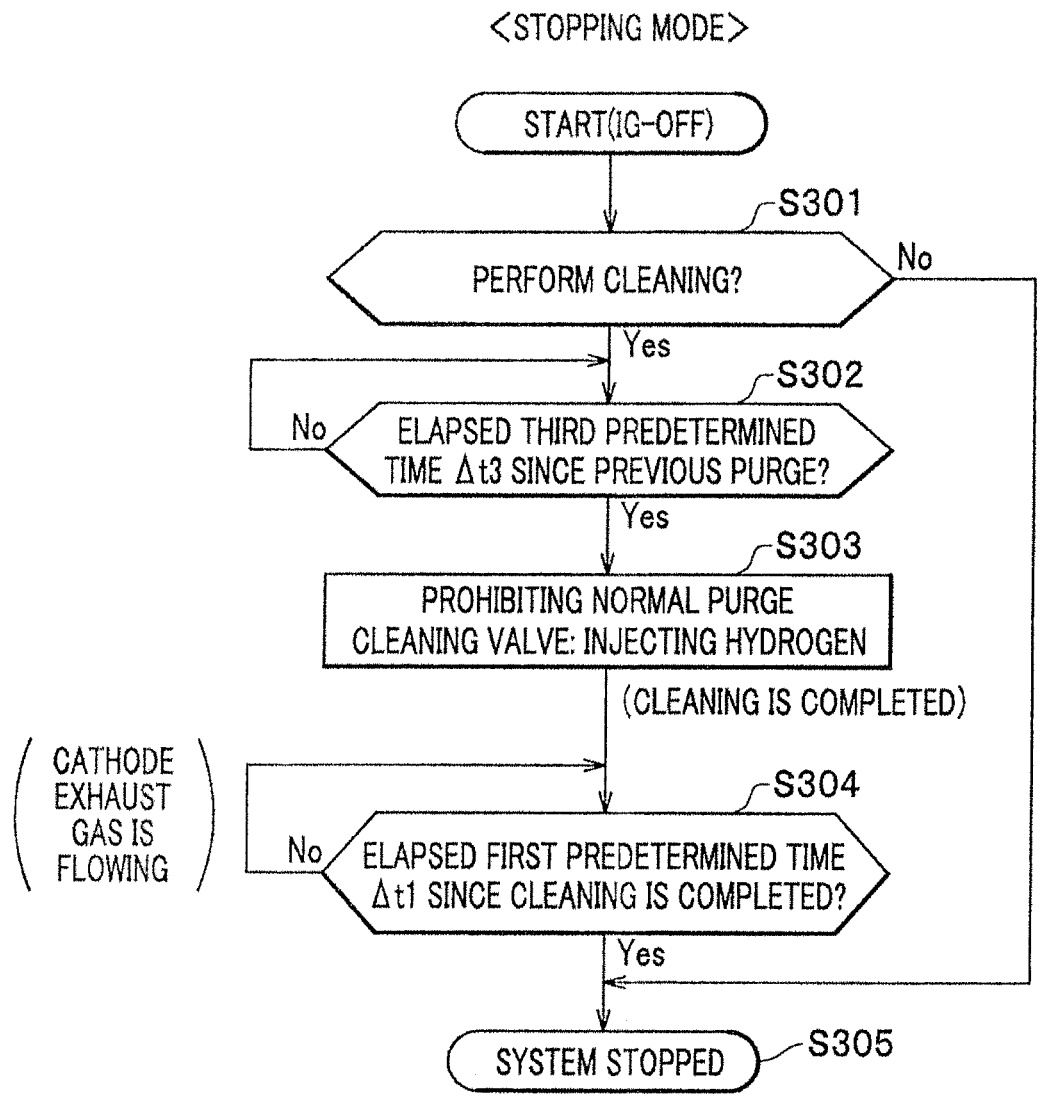
FIG. 11 is a flowchart showing a motion of the fuel cell vehicle according to the embodiment in a stopping mode.

In addition, when the IG 141 is turned OFF, the ECU 150 detects an OFF signal and starts a process shown in FIG. 11. Also, the ECU 150 controls a power generation controller (not shown) connected to an output terminal of the fuel cell stack 110, and stops power generation by the fuel cell stack 110.

In step S301, like steps S102 and S202, the ECU 150 determines whether the cleaning of the detection element 21 (the hydrogen sensor 10A) is needed to be performed or not (the sensitivity recovery is required or not).

If it is determined that the cleaning is needed to be performed (S301: Yes), the process of the ECU 150 proceeds to step S302. On the other hand, if it is determined that the cleaning is not needed to be performed (S301: No), the process of the ECU 150 proceeds to step S305.

In step S302, like steps S103 and S203, the ECU 150 determines whether the third predetermined time Δt3 has elapsed since the previous purge.

If it is determined that the third predetermined time Δt3 has elapsed (S302: Yes), the process of the ECU 150 proceeds to step S303. On the other hand, if it is determined that the third predetermined time Δt3 has not elapsed (S302: No), the ECU 150 repeats the judge in step S302.

In step S303, like steps S104 and S204, the ECU 150 prohibits the normal purge. That is, the ECU 150 prohibits opening the purge valve 123, and keeps the purge valve 123 closed, opens the cleaning valve 124 at the open time, and performs the cleaning of the hydrogen sensor 10A.

In step S304, like steps S105 and S205, the ECU 150 determines whether the first predetermined time Δt1 has elapsed since the cleaning in step S303 is completed.

If it is determined that the first predetermined time Δt1 has elapsed (S304: Yes), the process of the ECU 150 proceeds to step S205.

On the other hand, if it is determined that the first predetermined time Δt1 has not elapsed (S304: No), the ECU 150 repeats the judgment in step S304. If the judgment in step S304 is repeated, the cathode exhaust gas (the dilution gas) flows through the first dilution unit D1 and the hydrogen concentration falls rapidly in the first dilution unit D1 since the ECU 150 operates the compressor 131 (the dilution gas flowing unit).

In step S305, a shutdown valve (not shown) of the pipe 121a is closed in accordance with commands from the ECU 150 so as to stop supplying the hydrogen. Also, the compressor 131 is stopped in accordance with commands from the ECU 150. In this way, the fuel cell vehicle 200 (the fuel cell system 100) is stopped.

<<Effect of Fuel Cell Vehicle>>

According to the fuel cell vehicle 200, following effects can be obtained.

If it is determined that the cleaning of the hydrogen sensor 10A is needed to be performed (if the sensitivity recovery is required), the cleaning valve 124 is opened so as to inject the hydrogen, the temperature of the detection element 21 is raised to or above the desorption temperature by the combustion heat of the hydrogen and the heat generated by supplying power, the silicon compound adhering to the detection element 21 is desorbed on purpose, and the detection sensitivity of the hydrogen can be recovered. Therefore, the hydrogen sensor 10A can detect the hydrogen concentration for a long time.

Since the temperature of the detection element 21 is raised to the standby temperature by supplying power to the detection element 21 and the standby temperature is set to a temperature obtained by subtracting a temperature rise caused by the combustion heat of the hydrogen at the time of cleaning from the desorption temperature, the temperature of the detection element 21 at the time of cleaning does not rise too much, and the electric power required for supplying power is made to be appropriate.

Since the cleaning is begun at the time when the first predetermined time Δt1 during which the hydrogen concentration in the first dilution unit D1 falls to a predetermined concentration has elapsed since the previous cleaning was completed (S105: Yes, S205: Yes, S304: Yes), the concentration of the hydrogen supplied to the detection element 21 is not too high, and the temperature of the detection element 21 is not unexpectedly raised by the combustion heat of the hydrogen.

Also, since the cleaning is repeated every second predetermined time Δt2 which is equal to or greater than the first predetermined time Δt1 (S201: Yes), the sensitivity of the hydrogen sensor 10A can be recovered every second predetermined time Δt2.

Since the cathode exhaust gas (the dilution gas) flows through the first dilution unit D1 until the first predetermined time Δt1 has elapsed since the cleaning was completed (S105: No, S205: No, S304: No), the hydrogen concentration in the first dilution unit D1 falls rapidly and the next cleaning can be executed.

Since the cleaning is begun after the third predetermined time Δt3 during which the hydrogen concentration in the first dilution unit D1 falls to the predetermined concentration has elapsed since the purge valve 123 was closed (S103: Yes, S201: Yes, S302: Yes), the concentration of the hydrogen supplied to the detection element 21 is not unexpectedly raised and the temperature of the detection element 21 is not unexpectedly raised by the combustion heat of the hydrogen.

<<Second Embodiment>>

Although one embodiment of the present invention has been explained, the present invention is not limited to the embodiment. For example, the present invention can be modified as follows.

Figure 14:
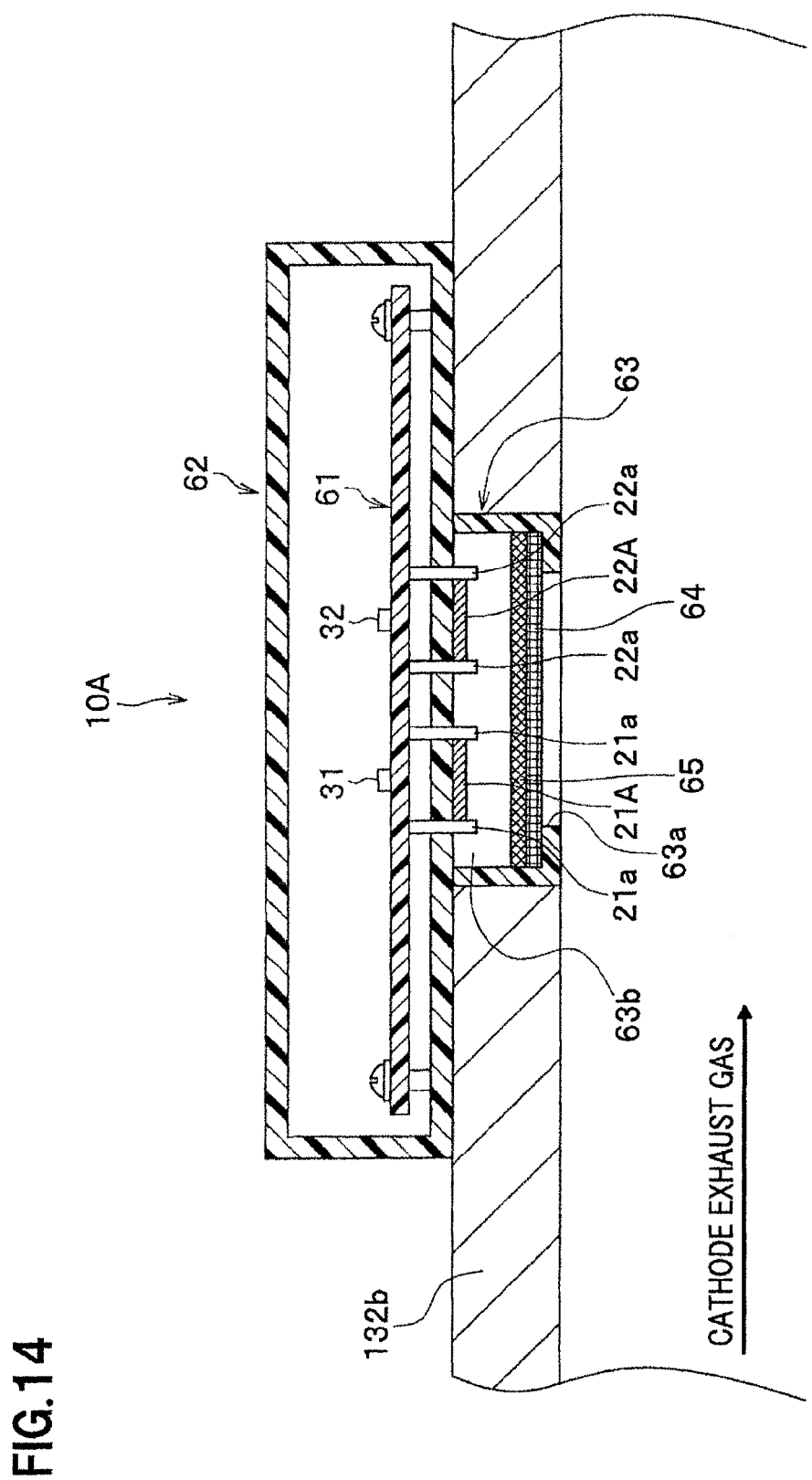
FIG. 14 is a side sectional view of a hydrogen sensor according to a second embodiment.

Although the detection element 21 made of the catalytic metal such as the platinum, etc., is coil shaped in the above embodiment (see FIG. 4), the shape of the detection element 21 is not limited to the coil shape. For example, as shown in FIG. 14, the detection element may be thin film shaped (a detection element 21A). In this way, the height of the housing 63 can be shortened and the hydrogen sensor 10A can be miniaturized. Also, if the detection element is thin film shaped, a surface area per unit volume of the detection element 21A is increased, a area which the hydrogen can contact is increased, and the temperature of the detection element 21A can be raised rapidly. In addition, in this case, the compensation element 22A is also thin film shaped.

Figure 15:
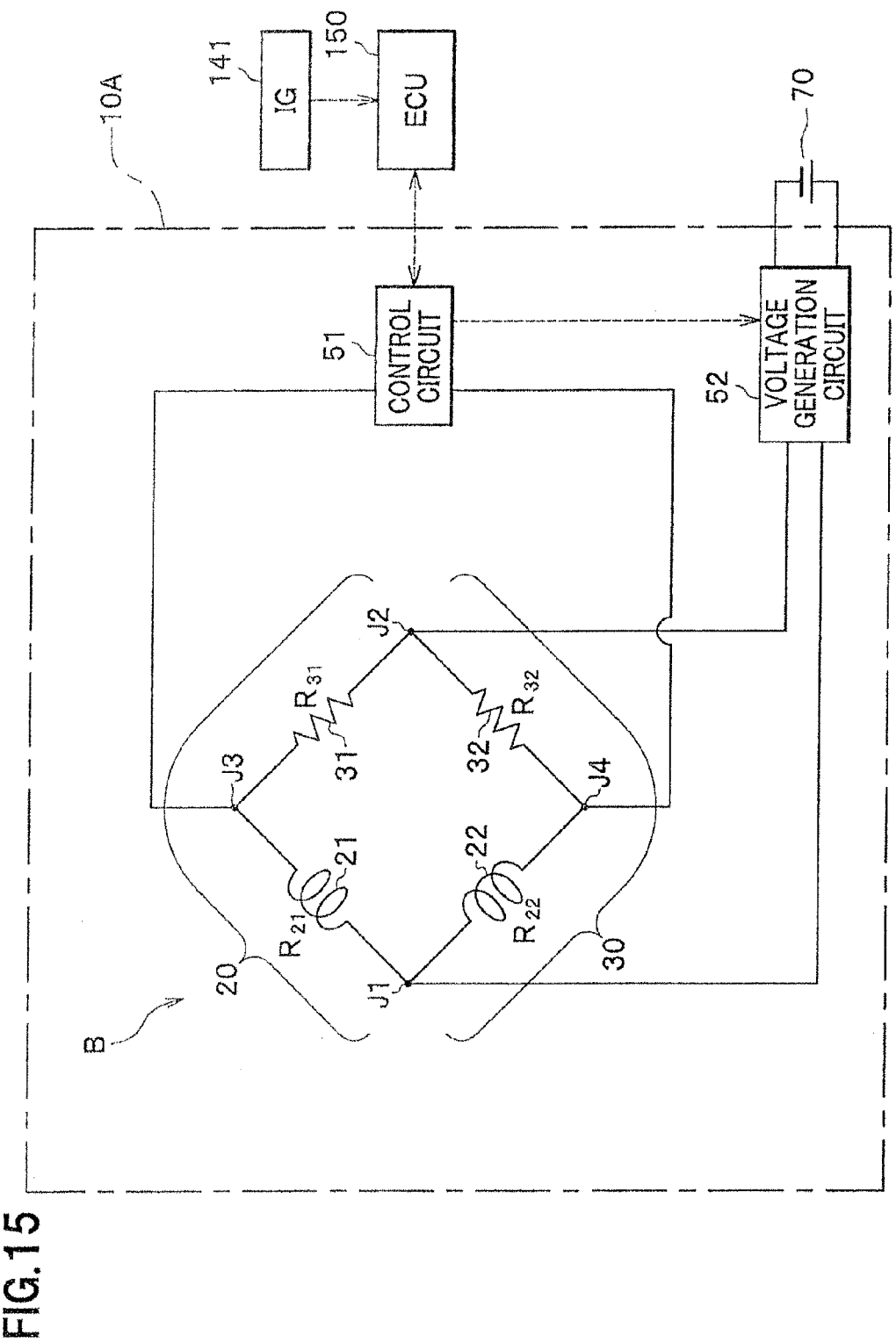
FIG. 15 is a circuit diagram of the hydrogen sensor according to the second embodiment.

Although the detection element 21 and the compensation element 22 are connected to the voltage generation circuit 52 in series in the above described embodiment, the detection element 21 and the compensation element 22 may be connected to the voltage generation circuit 52 in parallel (see FIG. 15). That is, in the bridge circuit B shown in FIG. 15, the first side 20 is formed by connecting the detection element 21 and the first resistor 31 in series, and the second side 30 is formed by connecting the compensation element 22 and the second resistor 32 in series.

Although the cleaning valve 124 (the valve unit) is composed of the gate valve, etc. which can keep the predetermined open state and the concentration of the hydrogen supplied to the detection element 21 is controlled by controlling the open time/close time of the cleaning valve 124 in the above described embodiment, for example, the cleaning valve 124 (the valve unit) may be composed of a butterfly valve, etc., whose opening degree can desirably adjustable, and the concentration of the hydrogen supplied to the detection element 21 is controlled by controlling the opening degree.

What is claimed is:

1. A hydrogen detection system, comprising:
a hydrogen sensor comprising an exposed detection element made of a catalytic metal, wherein the exposed detection element burns hydrogen so as to generate combustion heat, and the hydrogen sensor detects a hydrogen concentration based on a detected value of the detection element, the value varies corresponding to the combustion heat;
a heating unit for heating the detection element;
a hydrogen storage unit for storing a high-concentration hydrogen;
a hydrogen guiding pipe for guiding the hydrogen from the hydrogen storage unit to the detection element;
a flow rate adjusting device which is attached to the hydrogen guiding pipe and adjusts a flow rate of the hydrogen;
a first dilution unit for diluting the hydrogen from the hydrogen storage unit with a dilution gas at a position between the flow rate adjusting device and the detection element; and
a controller for controlling the heating unit and the flow rate adjusting device, wherein
the controller performs a sensitivity recovery process by controlling a concentration of hydrogen supplied from the first dilution unit to the detection element using the flow rate adjusting device so that a temperature of the detection element heated by the heating unit is equal to or greater than a desorption temperature at which silicon adhering to the detection element is desorbed by the combustion heat of the hydrogen when a sensitivity recovery of the hydrogen sensor is required.

2. The hydrogen detection system according to claim 1, wherein
the controller commands the heating unit to heat the detection element to a standby temperature, and
the standby temperature is a temperature obtained by subtracting a temperature rise caused by a combustion of the hydrogen at the time of requirement of the sensitivity recovery from the desorption temperature.

3. The hydrogen detection system according to claim 1, wherein
the hydrogen sensor comprises a power supplying unit for supplying power to the detection element, and detects the hydrogen concentration based on an increase in a resistor value of the detection element caused by the combustion of the hydrogen, and
the heating unit comprises the power supplying unit, and the temperature of the detection element is raised by supplying power to the detection element.

4. The hydrogen detection system according to claim 1, wherein
the flow rate adjusting device is provided with a valve unit capable of keeping a predetermined open state, and
the controller controls the concentration of the hydrogen supplied to the detection element by controlling an open time/close time of the valve unit.

5. The hydrogen detection system according to claim 1, wherein
the flow rate adjusting device is provided with the valve unit whose opening degree can be desirably adjusted, and
the controller controls the concentration of the hydrogen supplied to the detection element by controlling the opening degree of the valve unit.

6. The hydrogen detection system according to claim 1, wherein the controller begins a present sensitivity recovery process after a first predetermined time during which the hydrogen concentration in the first dilution unit falls to a predetermined concentration has elapsed since a previous sensitivity recovery process was completed.

7. The hydrogen detection system according to claim 6, wherein the controller repeats the sensitivity recovery process every second predetermined time which is equal to or greater than the first predetermined time.

8. The hydrogen detection system according to claim 1, further comprising a dilution gas flowing unit for flowing the dilution gas through the first dilution unit, and the controller commands the dilution gas flowing unit to supply the dilution gas after the sensitivity recovery process was completed.

9. The hydrogen detection system according to claim 1, wherein
the hydrogen sensor is attached to a cathode exhaust gas flow path through which a cathode exhaust gas is supplied from a cathode of the fuel cell,
the hydrogen guiding pipe joins the cathode exhaust gas flow path which is upstream of the hydrogen sensor,
the first dilution unit is the cathode exhaust gas flow path between the hydrogen guiding pipe and the hydrogen sensor, and
the dilution gas is the cathode exhaust gas.

10. The hydrogen detection system according to claim 9, wherein
an anode exhaust gas flow path which exhausts an anode exhaust gas supplied from an anode of the fuel cell joins the cathode exhaust gas flow path which is upstream of the hydrogen guiding pipe,
the anode exhaust gas flow path is provided with a purge valve which is open when the anode exhaust gas is exhausted, and
the controller begins the sensitivity recovery process after a third predetermined time during which the hydrogen concentration in the first dilution unit falls to a predetermined concentration has elapsed since the purge valve was closed.

11. The hydrogen detection system according to claim 9, wherein the cathode exhaust gas flow path which is downstream of the hydrogen sensor is provided with a second dilution unit.

12. The hydrogen detection system according to claim 1, wherein
the hydrogen sensor is placed in a space opened to the atmosphere,
the first dilution unit is a space for dilution opened to the atmosphere and which is placed between a downstream end of the hydrogen guiding pipe and the hydrogen sensor, and
the dilution gas is the atmosphere.

13. The hydrogen detection system according to claim 1, wherein
the hydrogen detection system is mounted on a fuel cell vehicle which has a fuel cell and is driven by an electric power generated by the fuel cell, and
the hydrogen storage unit supplies the hydrogen to the fuel cell as the fuel gas.

* * * * *